(12) United States Patent
Hahn et al.

(10) Patent No.: US 10,780,278 B2
(45) Date of Patent: Sep. 22, 2020

(54) INTEGRATED MULTI-DEVICE CARDIAC RESYNCHRONIZATION THERAPY USING P-WAVE TO PACE TIMING

(71) Applicant: CARDIAC PACEMAKERS, INC., St. Paul, MN (US)

(72) Inventors: Stephen J. Hahn, Shoreview, MN (US); Krzysztof Z. Siejko, Maple Grove, MN (US); Amy Jean Brisben, St. Paul, MN (US); Keith R. Maile, Jr., New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 265 days.

(21) Appl. No.: 15/684,366

(22) Filed: Aug. 23, 2017

(65) Prior Publication Data

US 2018/0056075 A1    Mar. 1, 2018

Related U.S. Application Data

(60) Provisional application No. 62/378,880, filed on Aug. 24, 2016.

(51) Int. Cl.
*A61N 1/365* (2006.01)
*A61N 1/372* (2006.01)
(Continued)

(52) U.S. Cl.
CPC ........ *A61N 1/36507* (2013.01); *A61B 5/0422* (2013.01); *A61B 5/0452* (2013.01);
(Continued)

(58) Field of Classification Search
None
See application file for complete search history.

(56) References Cited

U.S. PATENT DOCUMENTS 3,835,864 A    9/1974 Rasor et al.
3,943,936 A    3/1976 Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — Brian T Gedeon
(74) *Attorney, Agent, or Firm* — Seager, Tufte & Wickhem LLP

(57) ABSTRACT

Methods, systems and devices for providing cardiac resynchronization therapy (CRT) to a patient using a leadless cardiac pacemaker (LCP) and an extracardiac device (ED). The LCP is configured to deliver pacing therapy at a pacing interval. Illustratively, the ED may be configured to analyze the cardiac cycle including a portion preceding the pacing therapy delivery for one or several cardiac cycles, and determine whether an interval from the P-wave to the pace therapy in the cardiac cycle(s) is in a desired range. In an example, if the P-wave to pace interval is outside the desired range, the ED communicates to the LCP to adjust the pacing interval.

20 Claims, 18 Drawing Sheets

(51) Int. Cl.
  *A61N 1/375*   (2006.01)
  *A61N 1/39*    (2006.01)
  *A61B 5/042*   (2006.01)
  *A61B 5/00*    (2006.01)
  *A61N 1/37*    (2006.01)
  *A61B 5/0452*  (2006.01)

(52) U.S. Cl.
  CPC .......... *A61B 5/4836* (2013.01); *A61N 1/365* (2013.01); *A61N 1/3702* (2013.01); *A61N 1/3756* (2013.01); *A61N 1/37264* (2013.01); *A61N 1/37288* (2013.01); *A61N 1/37512* (2017.08); *A61N 1/3925* (2013.01); *A61N 1/39622* (2017.08)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |

(56) References Cited

U.S. PATENT DOCUMENTS

| | | |
|---|---|---|
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |

(56) References Cited

U.S. PATENT DOCUMENTS

| | | |
|---|---|---|
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Heltinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 1,809,441 A1 | 10/2010 | Kane et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |

(56) References Cited

U.S. PATENT DOCUMENTS

| | | |
|---|---|---|
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |

(56) References Cited

U.S. PATENT DOCUMENTS

| | | |
|---|---|---|
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 * | 10/2017 | Sambelashvili ..... A61N 1/3688 |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,350,417 B2 * | 7/2019 | Cao ..................... A61B 5/0456 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |

(56) References Cited

U.S. PATENT DOCUMENTS

| | | |
|---|---|---|
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |

(56) References Cited

U.S. PATENT DOCUMENTS

| | | |
|---|---|---|
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |

(56) References Cited

U.S. PATENT DOCUMENTS

| | | |
|---|---|---|
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321011 A1 | 11/2015 | Carney et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |

(56) References Cited

FOREIGN PATENT DOCUMENTS

| | | |
|---|---|---|
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Wegmüller, "Intra-Body Communication for Biomedical Sensor Networks," Diss. ETH, No. 17323, 1-173, 2007.

Spickler et al., "Totally Self-Contained Intracardiac Pacemaker," Journal of Electrocardiology, vol. 3(3&4): 324-331, 1970.

Seyedi et al., "A Survey on Intrabody Communications for Body Area Network Application," IEEE Transactions on Biomedical Engineering, vol. 60(8): 2067-2079, 2013.

International Search Report and Written Opinion dated Nov. 21, 2017 for International Application No. PCT/US2017/048199.

\* cited by examiner

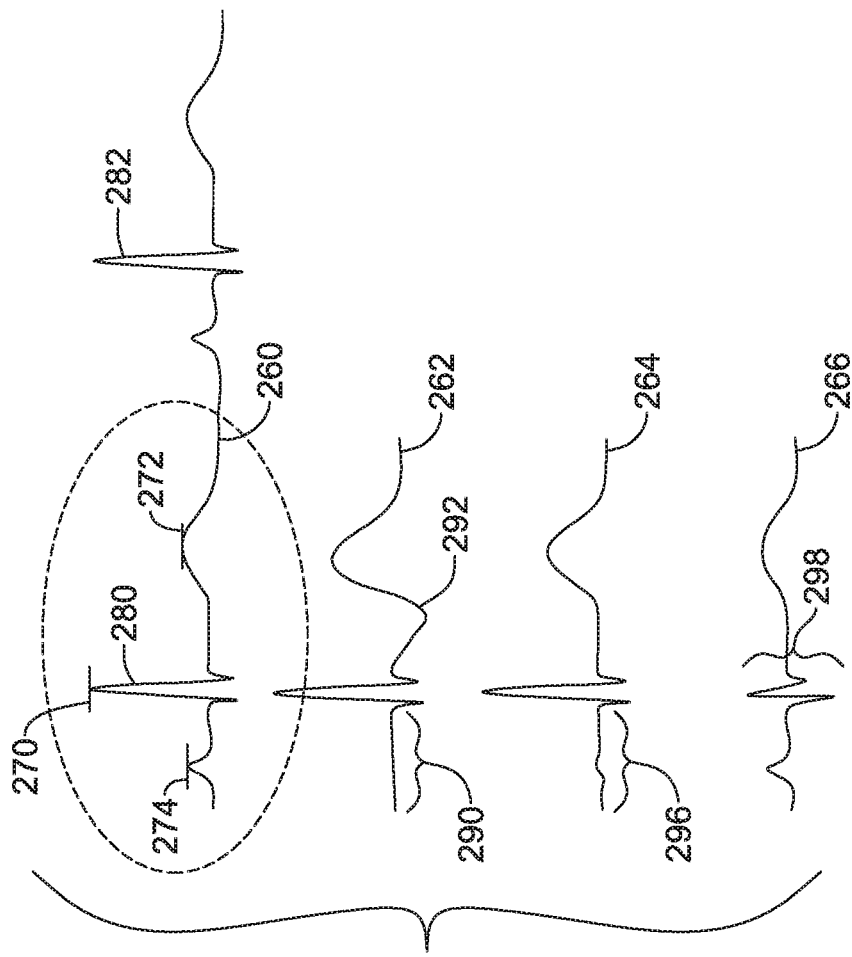
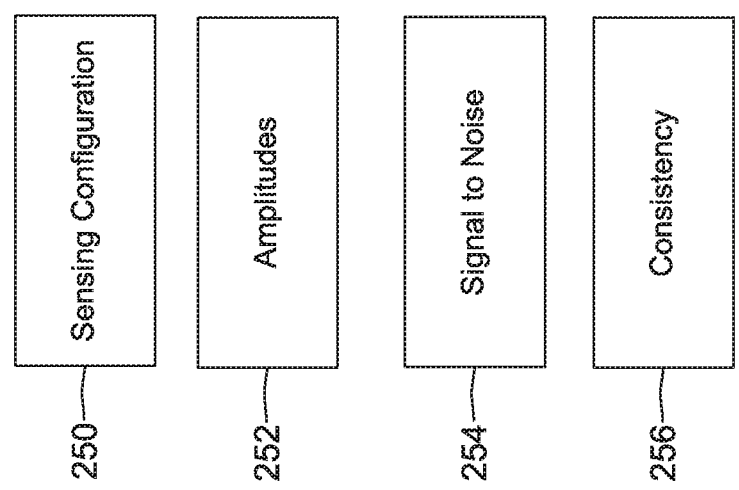
Figure 5

INTEGRATED MULTI-DEVICE CARDIAC RESYNCHRONIZATION THERAPY USING P-WAVE TO PACE TIMING

CROSS REFERENCE TO RELATED APPLICATIONS

The present application claims the benefit of and priority to U.S. Provisional Patent Application Ser. No. 62/378,880, filed Aug. 24, 2016, the disclosure of which is incorporated herein by reference.

BACKGROUND

Cardiac resynchronization therapy (CRT) modifies the electrical activation and contractions of the heart's chambers to enhance pumping efficiency. Benefits may include increased exercise capacity and reduced hospitalization and mortality. More particularly, CRT devices operate by affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same cardiac tissue at the same time. For example, electrical fusion between pacing of one ventricle with spontaneous activation of another ventricle (for example, paced left ventricular (LV) activation and intrinsic right ventricular (RV) activation) produces a fusion beat. The generation of fusion beats is a goal of CRT in many circumstances.

Prior systems generally include intracardiac electrodes coupled via transvenous leads to an implanted pulse generator. The leads of such systems are widely known as introducing various morbidities and are prone to eventual conductor and/or insulator failure. Such issues likely reduce usage of CRT within the indicated population of heart failure patients.

Such prior lead systems typically include ventricular and atrial components to facilitate sensing of atrial and ventricular events to enhance CRT timing. For example, in some patients, CRT may be achieved by pacing the left ventricle at a specific time relative to detection of an atrial event. The atrial signal may conduct to the right ventricle (RV) via natural conduction to generate an RV contraction, with paced LV contraction occurring at a desirable time relative to the RV contraction to yield a fusion beat. The interval from the atrial sensed event to the LV pace may be adjusted to enhance cardiac response in prior systems.

Newer generation pacemakers include the leadless cardiac pacemaker (LCP), which can be implanted entirely within the heart and does not require a transvenous (or any) lead. Such devices are commercially available on a limited basis, but are currently indicated for and capable of use in only bradycardia pacing. With further enhancements, the LCP also presents an opportunity to provide an alternative to traditional CRT using transvenous leads. New and alternative systems, devices and methods directed at providing CRT using the LCP are desired.

OVERVIEW

The present inventors have recognized, among other things, that a problem to be solved is that the absence of an intracardiac lead makes detection of an atrial event for purposes of CRT potentially difficult for a system using one or more ventricular LCP devices. U.S. Provisional Patent Application Ser. No. 62/355,121, the disclosure of which is incorporated herein by reference, suggests certain methods that may use an extracardaic device (such as a subcutaneous cardiac monitor (SCM), a subcutaneous implantable cardiac defibrillator (SICD), or a substernal variant of the SICD) to detect P-waves and provide timing information for use by an LCP. In some patients, however, P-waves may be difficult to detect or highly variable as sensed in the far field by an SCM or SICD, making reliance on P-wave detection possibly difficult.

As an alternative to reliance on atrial event detection, the present invention is directed at a different approach. An LCP is configured to provide pacing therapy using a Pace to Pace interval. A second device analyzes the cardiac signals around the pacing therapy delivery and determines a P-wave to Pace interval. The second device may communicate with the LCP to modify timing of the Pace to Pace intervals to achieve beneficial CRT therapy.

A first non-limiting example takes the form of a method of providing cardiac pacing therapy to a patient comprising: delivering pacing pulses using a Pace to Pace interval, the pacing pulses delivered by a first device; monitoring cardiac activity in a second device; and adjusting the Pace to Pace interval.

Additionally or alternatively, a second non-limiting example takes the form of a method as in the first non-limiting example, wherein the step of monitoring cardiac activity in a second device includes identifying a P-wave relative to the at least one of the pacing pulses, and the method further comprises: calculating a P-wave to Pace interval using at least the cardiac signals monitored by the second device; determining whether the P-wave to Pace interval is in the predetermined range and: if the P-wave to pace interval is above the predetermined range, communicating to the first device to shorten the Pace to Pace interval; and if the P-wave to pace interval is below the predetermined range, communicating to the first device to extend the Pace to Pace interval.

Additionally or alternatively, a third non-limiting example takes the form of a method as in the second non-limiting example, wherein analysis of the P-wave to pace interval is performed by the second device: detecting a pace pulse delivery by the first device; and searching a predetermined window prior to the detected pace pulse delivery for the P-wave.

Additionally or alternatively, a fourth non-limiting example takes the form of a method as in the second non-limiting example, wherein analysis of the P-wave to pace interval is performed by the second device: receiving a communication from the first device indicating at time of delivery of a pace pulse; and searching a predetermined window prior to the communicated time of delivery of the pace pulse for the P-wave.

Additionally or alternatively, a fifth non-limiting example takes the form of a method as in the second non-limiting example, wherein analysis of the P-wave to pace interval is performed by the second device: detecting an R-wave in the cardiac signal; searching a predetermined window prior to the R-wave for the P-wave and finding the P-wave; and communicating to the first device a time of the found P-wave.

Additionally or alternatively, a sixth non-limiting example takes the form of a method as in the second non-limiting example, wherein analysis of the P-wave to pace interval makes use of a composite of several cardiac cycles captured by the second device.

Additionally or alternatively, a seventh non-limiting example takes the form of a method as in the second non-limiting example, wherein analysis of the P-wave to pace interval makes use of an electrical cardiac signal captured for a single cardiac cycle.

Additionally or alternatively, an eighth non-limiting example takes the form of a method as in any of the second to seventh non-limiting examples, further comprising setting the predetermined range by calculating a P-R interval for an intrinsic cardiac cycle or cycles of the patient and selecting the predetermined range as a fraction of the P-R interval.

Additionally or alternatively, a ninth non-limiting example takes the form of a method as in any of the second to seventh non-limiting examples, further comprising setting the predetermined range by: delivering a plurality of pacing pulses at a plurality of P-wave to Pace intervals; determining which of the plurality of pacing pulses causes a desired cardiac response; and selecting a target P-wave to Pace interval corresponding to the desired cardiac response.

Additionally or alternatively, a tenth non-limiting example takes the form of a method as in the ninth non-limiting example, wherein the desired cardiac response is a fusion beat.

Additionally or alternatively, an eleventh non-limiting example takes the form of a method as in any of the first to tenth non-limiting examples, wherein the first device is a leadless cardiac pacemaker implanted in or on the left ventricle of the patient's heart, and the second device is a subcutaneous implantable defibrillator.

Additionally or alternatively, a twelfth non-limiting example takes the form of a method as in any of the first to tenth non-limiting examples, wherein the first device is a leadless cardiac pacemaker implanted in or on the left ventricle of the patient's heart, and the second device is a substernal implantable defibrillator.

Additionally or alternatively, a thirteenth non-limiting example takes the form of a method as in any of the first to tenth non-limiting examples, wherein the first device is a leadless cardiac pacemaker implanted in or on the left ventricle of the patient's heart, and the second device is a subcutaneous implantable cardiac monitor.

Additionally or alternatively, a fourteenth non-limiting example takes the form of a method as in any of the first to thirteenth first non-limiting examples, wherein the pace pulse delivery is performed to achieve a cardiac resynchronization therapy function.

Additionally or alternatively, a fifteenth non-limiting example takes the form of a method as in any of the first to thirteenth the first non-limiting examples, wherein the pace pulse delivery is performed to effect fusion beats.

A sixteenth non-limiting example take the form of an implantable medical device (IMD) configured for use as part of a cardiac therapy system comprising a leadless cardiac pacemaker (LCP) and the IMD, the IMD comprising: a plurality of electrodes for sensing cardiac activity; and operational circuitry configured to receive sensed cardiac signals from the plurality of electrodes and analyze cardiac activity as follows: determine when pace therapy is delivered by the LCP; analyze a segment of the sensed cardiac signals from the plurality of electrodes including a time period prior to pace therapy delivery from the LCP and calculate a P-wave to Pace interval; determine whether the P-wave to Pace interval is in a desired range, and, if the P-wave to Pace interval is not in the desired range, modifying a Pace to Pace interval that determines timing of the LCP pacing therapy.

Additionally or alternatively, a seventeenth non-limiting example takes the form of an IMD as in the sixteenth non-limiting example, wherein the operational circuitry is further configured to set the desired range by sensing a one or more intrinsic cardiac cycles, calculating a P-R interval of the patient's cardiac rhythm, and selecting the desired range as a fraction of the P-R interval.

Additionally or alternatively, an eighteenth non-limiting example takes the form of an IMD as in the sixteenth non-limiting example, wherein the operational circuitry is further configured to set the desired range by sensing a plurality of cardiac cycles paced by the LCP at differing P-wave to Pace intervals, determining which of the plurality of cardiac cycles has been paced in a manner that causes a desired cardiac response; and selecting a the desired range using a P-wave to Pace interval corresponding to the desired cardiac response.

Additionally or alternatively, a nineteenth non-limiting example takes the form of an IMD as in the eighteenth non-limiting example, wherein the desired response is a fusion beat.

Additionally or alternatively, a twentieth non-limiting example takes the form of an IMD as in the sixteenth non-limiting example, wherein the operational circuitry is configured to determine when pace therapy is delivered by the LCP by sensing the delivery of pace therapy using the plurality of electrodes.

Additionally or alternatively, a twenty-first non-limiting example takes the form of an IMD as in the sixteenth non-limiting example, wherein the operational circuitry is configured to determine when pace therapy is delivered by the LCP by receiving a communication from the LCP indicating that a pace therapy has been delivered.

Additionally or alternatively, a twenty-second non-limiting example takes the form of an IMD as in the twenty-first non-limiting example, wherein the operational circuitry is further configured to store a portion of the sensed cardiac signals for retrospective review following a determination that the pace therapy was delivered, and to analyze the segment of the sensed cardiac signals retrospectively using the stored portion.

Additionally or alternatively, a twenty-third non-limiting example takes the form of an IMD as in the sixteenth non-limiting example, wherein the desired range for the P-wave to Pulse interval is set such that the pacing therapy will cause fusion beats.

Additionally or alternatively, a twenty-fourth non-limiting example takes the form of an IMD as in the sixteenth non-limiting example, wherein the operational circuitry is configured to communicate an adjustment to a Pace to Pace interval to modify the therapy parameter of the LCP.

Additionally or alternatively, a twenty-fifth non-limiting example takes the form of a subcutaneous implantable defibrillator comprising therapy delivery circuitry configured for delivering defibrillation stimulus to a patient taking the form of an IMD as in any of the sixteenth to twenty-fourth non-limiting examples.

Additionally or alternatively, a twenty-sixth non-limiting example takes the form of a subcutaneous implantable monitoring device further taking the form of IMD as in any of the sixteenth to twenty-fourth non-limiting examples.

A twenty-seventh non-limiting example takes the form of an implantable leadless cardiac pacemaker (LCP) configured to operate in coordination with an extracardiac device (ED), comprising: a plurality of electrodes for delivering pacing therapy; communication circuitry configured to send and receive messages with the ED; operational circuitry configured to: deliver a pacing pulse using a Pace to Pace interval relative to a previously delivered pacing pulse; receive a message from the ED indicating a time at which a P-wave occurred in relation to a paced cardiac event; calculate a P-wave to Pace interval for the paced cardiac event; analyze the P-wave to Pace interval relative to a desired range; and: if the P-wave to pace interval is longer than a first threshold defining the range, shorten the Pace to Pace interval; or if the P-wave to pace interval is shorter than a second threshold defining the range, extend the Pace to Pace interval.

Additionally or alternatively, a twenty-eighth non-limiting example takes the form of an LCP as in the twenty-seventh non-limiting example, wherein the desired range for the P-wave to Pulse interval is set such that the pacing therapy will cause fusion beats.

A twenty-ninth non-limiting example takes the form of an implantable medical device system comprising: an implantable leadless cardiac pacemaker (LCP) configured to operate in coordination with an extracardiac device (ED), comprising: a plurality of electrodes for delivering pacing therapy; communication circuitry configured to send and receive messages with the ED; and operational circuitry to control pacing therapy delivery via the electrodes and manage the communication circuitry; an ED comprising a plurality of electrodes for sensing cardiac activity and communications circuitry for communicating with the LCP; wherein the system is configured to: deliver pacing therapy with the LCP according to a Pace to Pace interval; using one or both of the ED and the LCP, calculate a P-wave to Pace interval associated with the delivered pacing therapy from the LCP; and with the ED and LCP cooperating with one another, adjust the Pace to Pace interval as follows: if the P-wave to pace interval is longer than a threshold, shorten the Pace to Pace interval; or if the P-wave to pace interval is shorter than a threshold, extend the Pace to Pace interval.

A thirtieth non-limiting example takes the form of a system as in the twenty-ninth non-limiting example, wherein the system is configured such that the P-wave to Pace interval is calculated by the ED detecting a pacing pulse and a P-wave preceding the pacing pulse, and the step of adjusting the Pace to Pace interval is performed by the LCP responding to a request or command from the ED.

A thirty-first non-limiting example takes the form of a system as in the twenty-ninth non-limiting example, wherein the system is configured such that the P-wave to Pace interval is calculated by the LCP communicating timing of a pacing pulse delivery to the ED and the ED determining a time at which a P-wave preceding the pacing pulse occurred, and the step of adjusting the Pace to Pace interval is performed by the LCP responding to a request or command from the ED.

A thirty-second non-limiting example takes the form of a system as in the twenty-ninth non-limiting example, wherein the system is configured such that the P-wave to Pace interval is calculated by the ED detecting a P-wave, and communicating timing of the P-wave to the LCP, and the LCP determining when the P-wave occurred relative to a pace pulse delivered by the LCP.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 illustrates selected factors for sensing configuration;

DETAILED DESCRIPTION

The following description should be read with reference to the drawings. The description and the drawings, which are not necessarily to scale, depict illustrative embodiments and are not intended to limit the scope of the disclosure.

Figure 1:
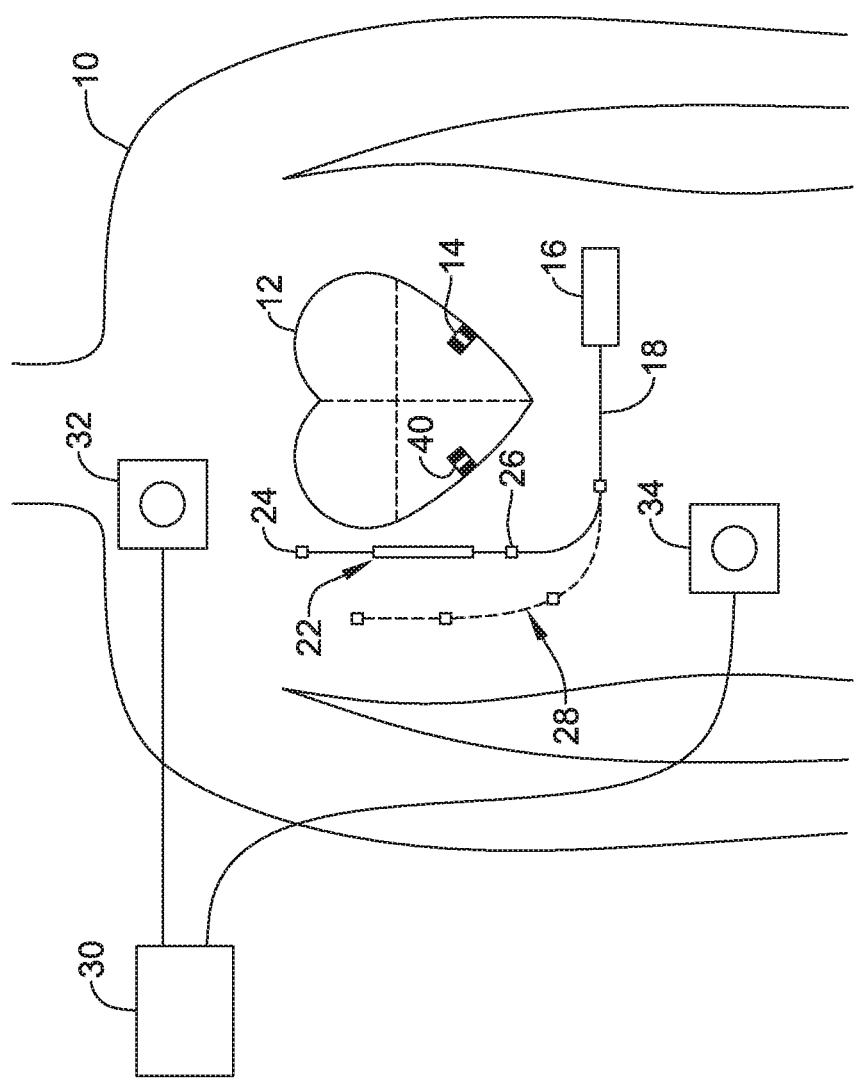
FIG. 1 illustrates a patient having a plurality of implantable medical devices.

FIG. 1 illustrates a patient 10 with a first implanted medical device, shown as a leadless cardiac pacemaker (LCP) 14 implanted inside the heart 12, in the left ventricle for illustrative purposes. The LCP 14 may be implanted in other chambers, such as the right ventricle or in the atrium, and more than one LCP may be provided.

A second medical device in the form of a subcutaneous implantable defibrillator (SICD) having a left axillary canister 16 and a lead 18 is also present. The illustrative lead 18 is shown with a defibrillation coil 22 and sensing electrodes 24, 26 distal and proximal of the coil 22. The lead 18 may optionally include a bifurcation 28 to provide an additional set of sensing or stimulus providing electrodes, if desired.

In some embodiments the lead may be as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Rather than bifurcation, plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE. Any suitable design for single, multiple, or bifurcated implantable leads may be used.

The lead 18 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANE- OUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

A substernal placement may be used instead, with one finger 18/20 or the entire distal end of the lead (that is, the end distant from the canister 16) going beneath the sternum. Some examples of such placement are described in US PG Patent Pub. No. 2017/0021159, titled SUBSTERNAL PLACEMENT OF A PACING OR DEFIBRILLATING ELECTRODE, the disclosure of which is incorporated herein by reference. Still another alternative placement is shown in US Provisional Patent Application No. 62/371,343, titled IMPLANTATION OF AN ACTIVE MEDICAL DEVICE USING THE INTERNAL THORACIC VASCULATURE, the disclosure of which is incorporated herein by reference.

The devices 14 and 16 may communicate with one another and/or with an external programmer 30 using conducted communication, in some examples. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver. RF or inductive communication may be used instead. Alternatively the devices 14 and 16 may communicate via inductive, optical, sonic, or RF communication, or any other suitable medium.

The programmer 30 may optionally use a wand (not shown) and/or skin electrodes 32 and 34 to facilitate communication. For example, skin electrodes 32 and 34 may be used for conducted communication with an implantable device. For other communication approaches such as RF or inductive communication, the programmer 30 may use a programming wand or may have an antenna integral with the programmer 30 housing for communication. Though not shown in detail, the programmer 30 may include any suitable user interface, including a screen, buttons, keyboard, touchscreen, speakers, and various other features widely known in the art.

Subcutaneous implantable defibrillators may include, for example, the Emblem SICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock.

In some examples, rather than a therapy device such as the SICD shown in FIG. 1, a second implantable medical device may take the form of an implantable monitoring device such as a subcutaneous cardiac monitor (SCM). An SCM may be, for example, a loop monitor that captures data under select conditions using two or more sensing electrodes on a housing thereof and/or attached thereto with a lead. Such monitors have found use to assist in diagnosing cardiac conditions that may be infrequent or intermittent, or which have non-specific symptoms. In the context of the present invention, an SCM, or even a wearable cardiac monitor, may be used in place of the SICD as described in any of the following examples.

Several examples focus on using a left ventricular LCP 14. However, some examples may instead use a right ventricular LCP 40, and other examples may include both the left ventricular LCP 14 and right ventricular LCP 40. In other examples, a three implant system may include two LCP devices 14, 40, as well as a subcutaneous device such as the SICD 16. In still other examples, an atrial-placed LCP (not shown) may also be included or may take the place of one of the ventricular LCP devices 14, 40.

Figure 2:
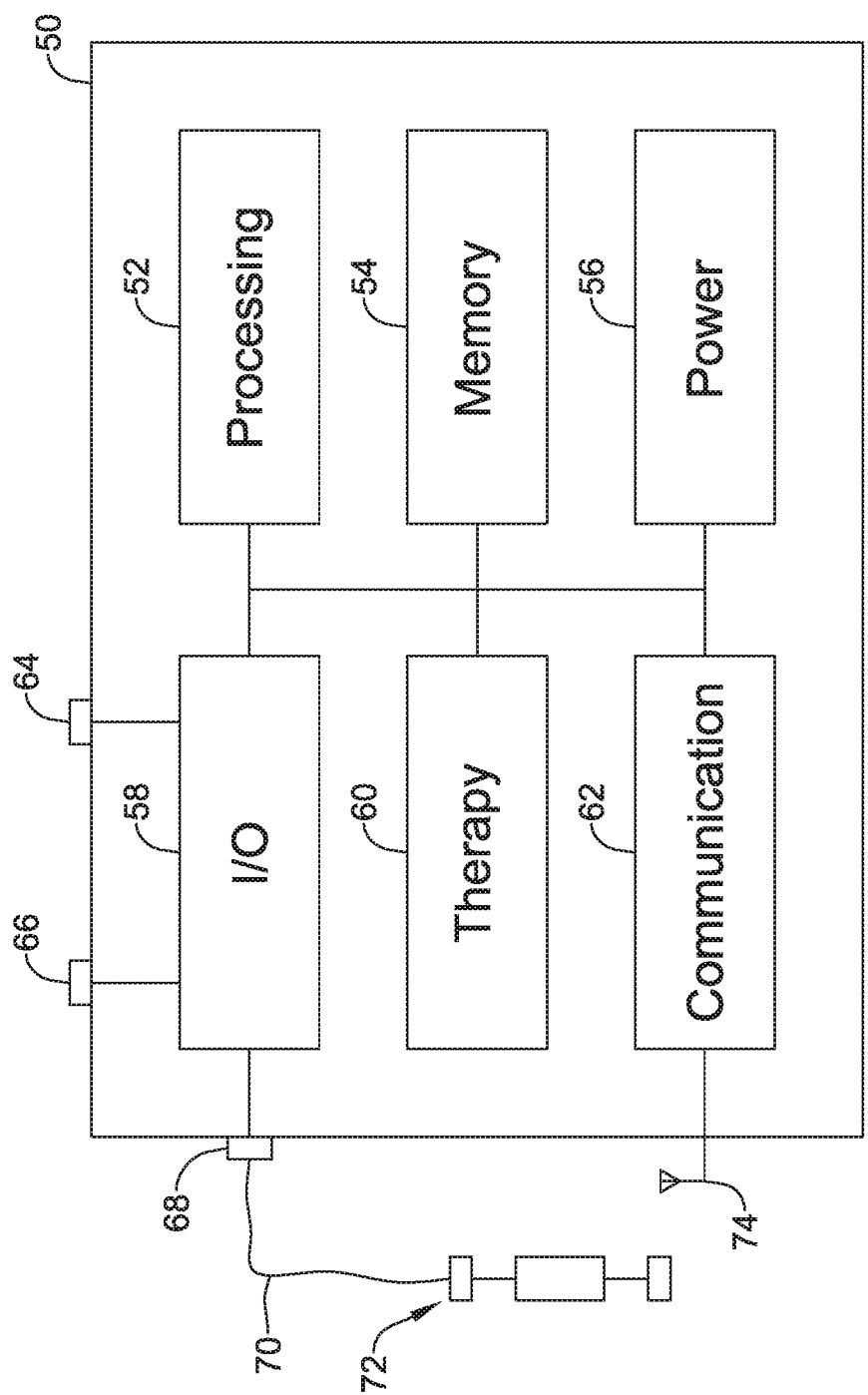
FIG. 2 shows an illustrative implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. These functional blocks make up the operational circuitry of the device. The I/O circuitry 58 can be coupled to one or more electrodes 64, 66 on the housing of the device 50, and may also couple to a header 68 for attachment to one or more leads 70 having additional electrodes 72.

The processing block 52 will generally control operations in the device 50 and may include a microprocessor or microcontroller and/or other circuitry and logic suitable to its purpose. A state machine may be included. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexors for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. A monitoring device may omit the therapy block 60 and may have a simplified I/O circuitry used simply to capture electrical or other signals such as chemical or motion signals.

The communication circuitry 62 may be coupled to an antenna 74 for radio communication (such as Medradio, ISM, or other RF), or alternatively to a coil for inductive communication, and/or may couple via the I/O circuitry 58 to a combination of electrodes 64, 66, 72, for conducted communication. Communication circuitry 62 may include a frequency generator/oscillator and mixer for creating output signals to transmit via the antenna 74. Some devices 50 may include a separate or even off-the shelf ASIC for the communications circuitry 62, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 64, 66, but may omit the header 68 for coupling to lead 70. In one example, a leadless device may use a header to couple to an electrode support feature that is attached to or wraps around the device housing.

Figure 3:
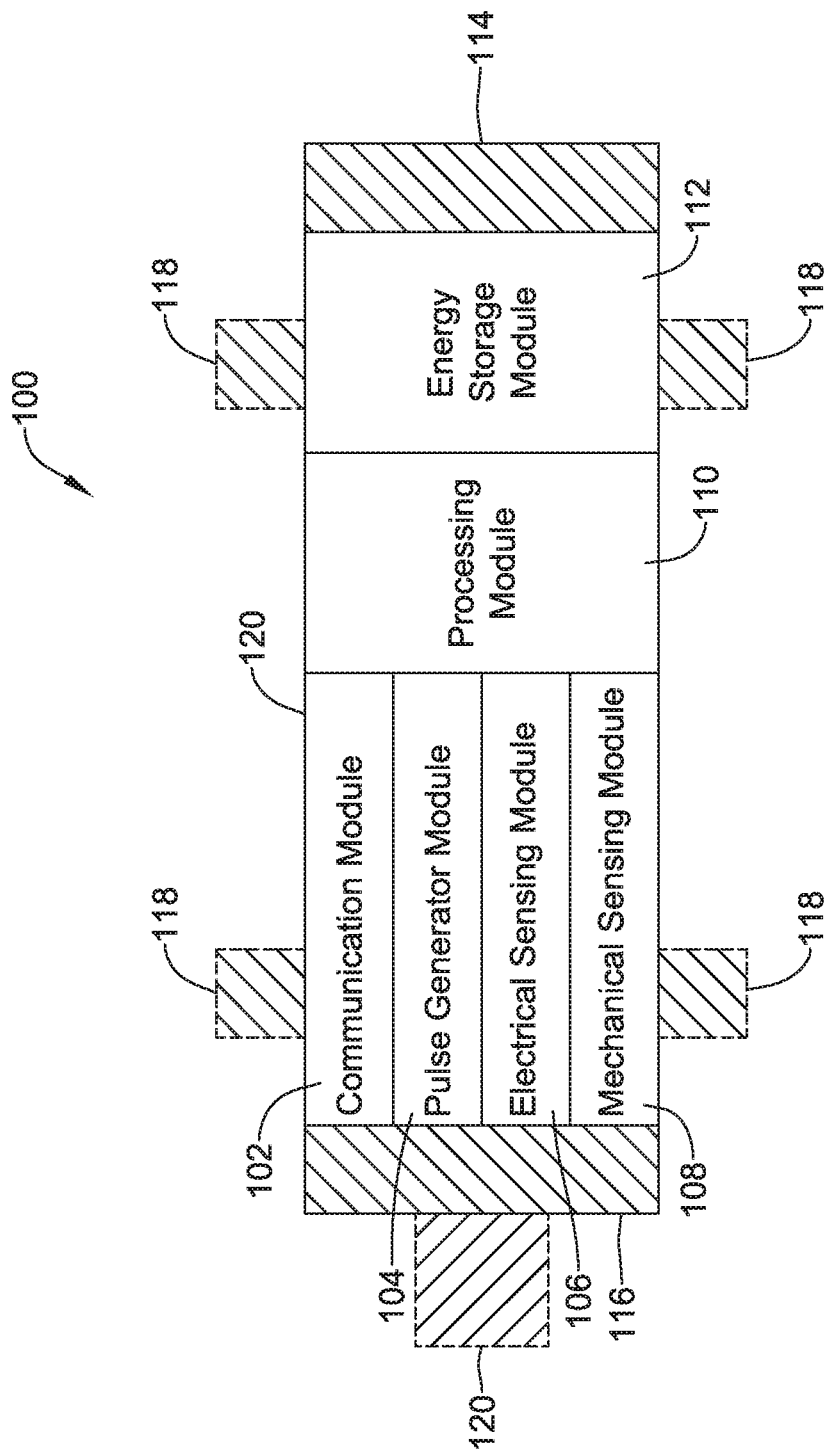
FIG. 3 shows an illustrative implantable leadless cardiac pacemaker.

FIG. 3 shows an illustrative LCP design. The LCP 100 is shown as including several functional blocks including a communications module 102, a pulse generator module 104, an electrical sensing module 106, and a mechanical sensing module 108. A processing module 110 may receive data from and generate commands for outputs by the other modules 102, 104, 106, 108. An energy storage module is highlighted at 112 and may take the form of a rechargeable or non-rechargeable battery, or a supercapacitor, or any other suitable element. Various details of the internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 114 and a second end electrode at 116. A number of tines 118 may extend from the device in several directions. The tines 118 maybe used to secure the device in place within a heart chamber. Another attachment structure is shown at 120 and may take the form of a helical screw, if desired. In some examples, tines 118 are used as the only attachment features. Tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Fixation and retrieval structures may instead resemble that of the Micra™ (Medtronic) or Nanostim™ (St. Jude Medical) leadless pacemakers.

Figure 4:
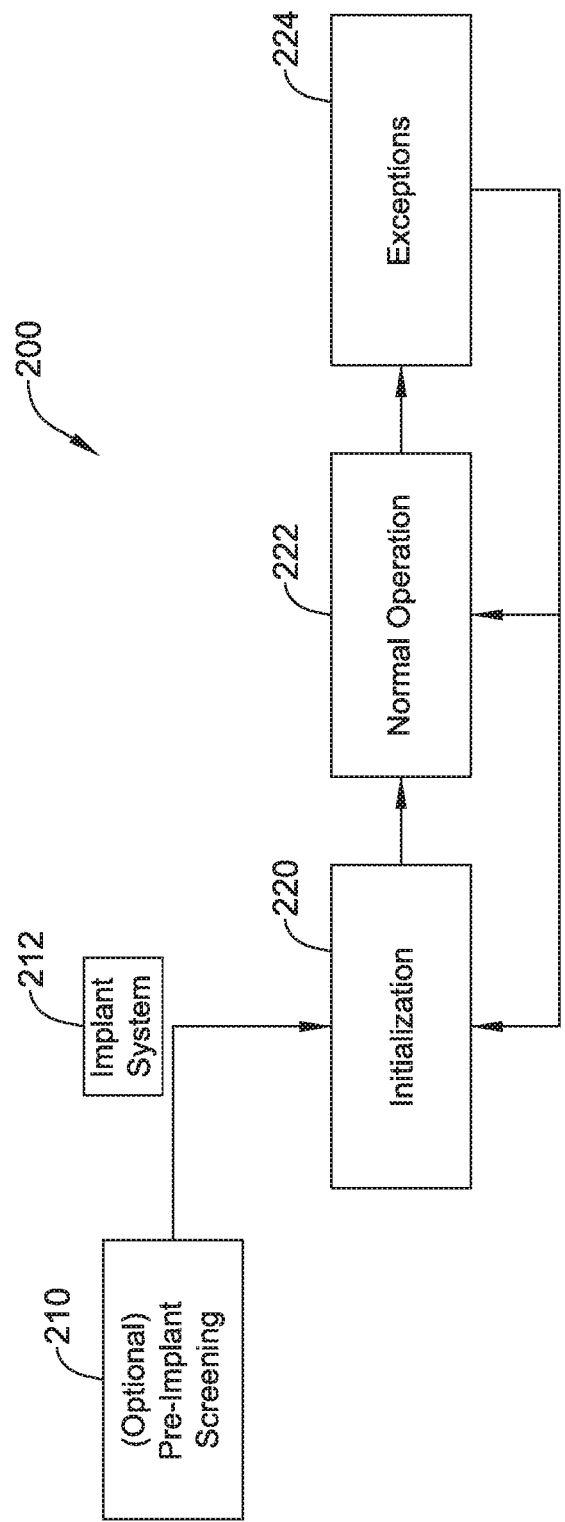
FIG. 4 shows an overall method of use of a system.

FIG. 4 shows an overall method of use of a system. The method 200 in this case goes back, optionally, to pre-implant screening, as indicated at 210. For example, the implantation of an SICD may occur following pre-implant screening for cardiac signal amplitude and/or signal to noise ratio, and/or to determine whether the patient's routine cardiac rhythm will be well managed using an SICD. Some example screening tools, metrics and methods discussed in U.S. Pat. No. 8,079,959, titled PATIENT SCREENING TOOLS FOR IMPLANTABLE CARDIAC STIMULUS SYSTEMS, and/or U.S. patent application Ser. No. 15/001,976, titled AUTOMATED SCREENING METHODS AND APPARATUSES FOR IMPLANTABLE MEDICAL DEVICES, the disclosures of which are incorporated herein by reference.

As noted in U.S. Provisional Patent Application 62/355,121, the disclosure of which is incorporated herein by reference, pre-implant screening may also determine whether the patient is well suited to have a combined LCP/SICD or LCP/SCM system for CRT by assessing the presence or absence of a P-wave. P-wave related screening may be optional with the present invention, as various examples rely on SICD or SCM analysis of the QRS complex (or other cardiac signal) to confirm fusion, rather than the appearance or timing of the P-wave, to enhance or control CRT to attain desirable fusion.

The system(s) are then implanted at 212. Implantation may include the placement of an LCP on or in the heart, as well as placement of an SCM or SICD elsewhere in the patient such as between the ribs and the skin. The system may undergo intraoperative testing as is known in the art for each of LCP, SCM and SICD devices, to ensure adequate sensing configurations and/or therapy capability.

Next, the system undergoes initialization, at 220. Initialization may include, for example, the setting of various sensing and other parameters. Examples of initialization may include selecting of a sensing vector or combination of sensing vectors, such as in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 SENSING VECTOR SELECTION IN A CARDIAC STIMULUS DEVICE WITH POSTURAL ASSESSMENT, the disclosures of which are incorporated herein by reference. Related concepts surrounding the use of multiple vector sensing are also disclosed in US PG Patent Pub. Nos. 2017/0112399, 2017/0113040, 2017/0113050, and 2017/0113053, the disclosures of which are incorporated herein by reference. Methods as discussed in US PG Patent Pub. No. 2017/0156617, titled AUTOMATIC DETERMINATION AND SELECTION OF FILTERING IN A CARDIAC RHYTHM MANAGEMENT DEVICE, the disclosure of which is incorporated herein by reference, may be used as well for setting filtering characteristics.

Thus, initialization may include methods for selecting a sensing vector as shown by FIG. 5, below. Initialization for an LCP may also include the setting of parameters for therapy including, for example, selecting pace shape, pulsewidth and/or amplitude. If plural LCPs are included in a system, the relative timing between pace deliveries amongst the plural LCPs, and other suitable features, may be set as well. Initialization may also include identifying a P-R interval for the patient, which can be done and used as discussed below relative to FIG. 6.

Once initialization 220 is completed, normal operation can occur as indicated at 222. Such operation may include CRT delivery in which a first device delivers pacing pulses using a Pace to Pace interval, and a second device monitors cardiac electrical signals to determine a P-wave to pace interval and determine whether the P-wave to Pace interval is in a desired range; if the P-wave to Pace interval is outside of the desired range, communication from the second device to the first device occurs to adjust the Pace to Pace interval.

In illustrative embodiments, the P-wave to Pace interval is calculated or measured retrospectively, by analysis of a time period that precedes the pace pulse delivery (for example, a period from 350 to 50 milliseconds before a pace pulse is delivered may be analyzed) and/or R-wave peak (for example, a period from 400 milliseconds to about 75 milliseconds before the R-wave peak may be analyzed). By "retrospective," the intended meaning is that the pace pulse of a given cardiac cycle occurs without reference to the P-wave for that cardiac cycle; retrospective analysis analyzes the cardiac cycle with the pace pulse either sensed within the cardiac cycle or superimposed thereon using known timing data, and analyzes the P-wave to pace pulse interval to determine whether to make an adjustment affecting a subsequent cardiac cycle. Various examples are shown below.

Figure 13:
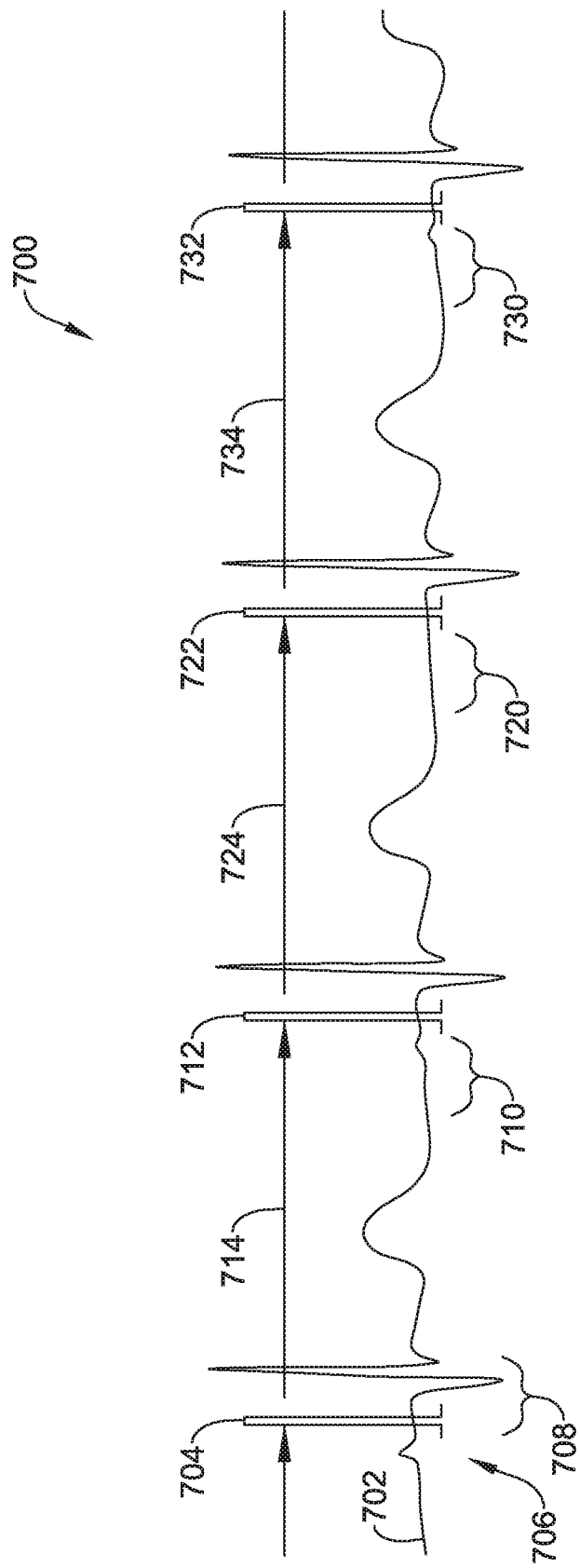
FIGS. 13-14 show illustrative exceptions.
Figure 14:
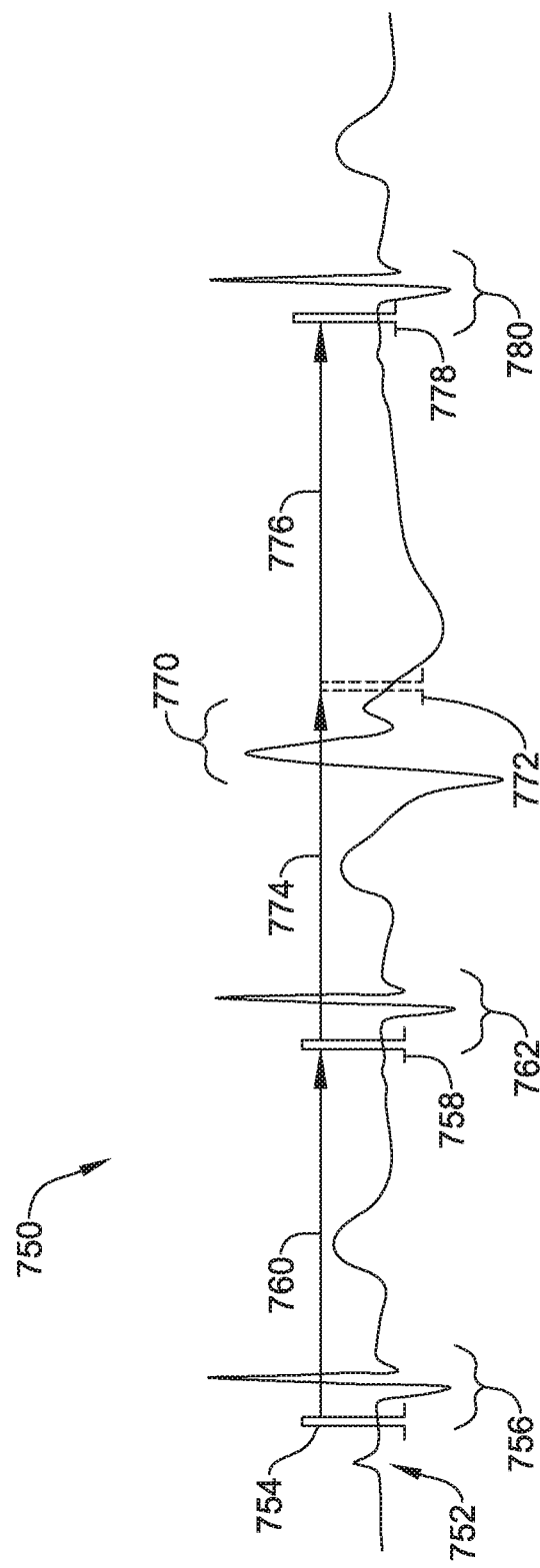

As needed, exceptions may be handled at 224. FIGS. 13-14, below, show certain exceptions and handling thereof. The exceptions 224 may allow return to normal operation 222 once handled, or may require re-initialization 220, or other processes or termination of the therapy in some circumstances.

FIG. 5 illustrates selected factors for sensing configuration. As illustrated at 250, sensing vector configuration may be performed during this part of the initialization of a system. The amplitudes of relevant cardiac signals and signal features may be used, as indicated at 252. Signal to noise ratio 254 may also be considered. The consistency 256, or lack thereof, of the cardiac signals captured using a particular sensing configuration (vector, filtering, gain, etc.) may be observed and used as well. For example, if the cardiac signal varies significantly in a given sensing vector from one cardiac complex to the next, that particular sensing vector may be rejected due to lack of consistency.

Selected factors 252, 254, 256 may be used to analyze a plurality of sensed signals along one or a number of cardiac sensing vectors. For example, as shown in FIG. 1, the SICD or SCM 16 may include an electrically active canister and a lead 18 having a number of electrodes 22, 24, 26, 28, and others shown but not numbered. Each pair of electrodes may define a sensing vector, with the different sensing vectors available having different characteristics given their position relative to the heart and each other. Signals vectors may be combined as well to yield further available sensing vectors.

The plural sensing vectors may provide different looking cardiac signals, as shown in FIG. 5 at 260, 262, 264, 266. Some have greater peak amplitudes, and some have signals with relative peaks that may represent noisier signals. The amplitudes 252 may include, for example, the amplitudes shown at 270 (R-wave peak), 272 (T-wave peak), and/or 274 (P-wave peak). Signal to noise ratio may be assessed by comparing the peak at 270 to those at 272 and/or 274, with lower ratios potentially making it harder to distinguish and accurately detect R-waves rather than the P-waves or T-waves. Alternatively, signal to noise ratio may be calculated by using statistical metrics and identified features (R-wave to root mean square voltage, for example).

Consistency for a given vector may be observed by, for example, comparing QRS complex at 280 to a subsequent QRS complex 282. More consistent QRS complex shape may be helpful to reliable and repeatable cardiac signal detection. In the example shown, as noted by the circle, the signal at 260 may be a preferred or selected sensing vector over the other signals 262, 264, 266, based on the QRS at 280 matching the QRS at 282, while also having large amplitude 270 both in absolute terms as well as when compared to the T-wave 272 and/or P-wave 274. These and/or other factors may be used to determine a sensing configuration.

Figure 6:
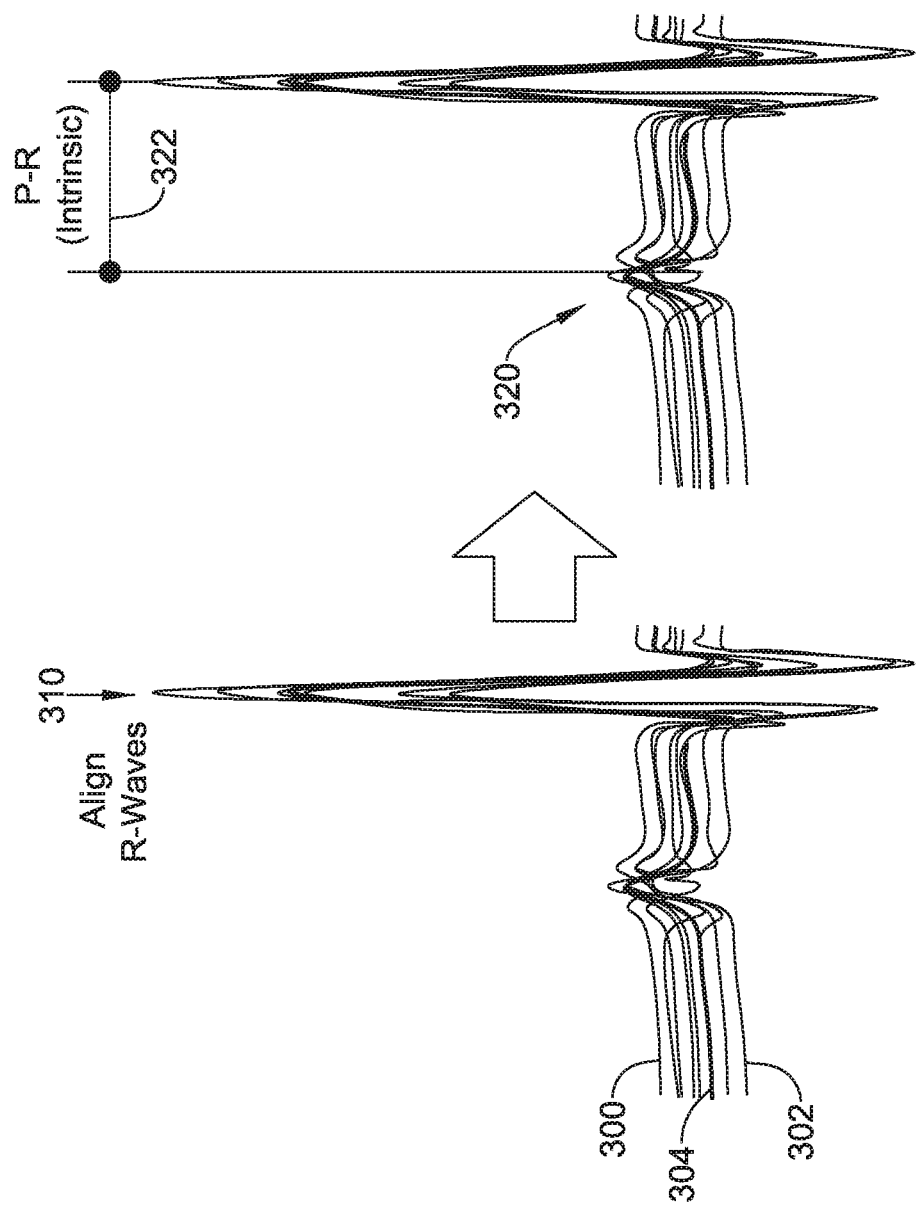
FIG. 6 illustrates a method of calculating a P-R interval for intrinsic heart beats.

FIG. 6 illustrates a method of calculating a P-R interval for intrinsic heart beats. In this examples, a plurality of electrical signals for a number of cardiac cycles are sensed and analyzed together; thus the Figure shows separate traces 300, 302, and a heavier line 304 represents the composite of the individual traces. The composite may be, for example, a point-by-point average or median of the individual traces or a smoothed version thereof.

For analysis of the P-R interval, as indicated at 310, the R-wave may be used as the fiducial for aligning the signals. Next, the composite signal is assessed to identify the peak for the P-wave across the composite, as indicated at 320. Point 320 may be the peak of the average of all the signals, or may be selected in some other manner such as by selecting the point of the highest median signal. In an alternative, the turning point of each signal 300, 302 most likely associated with the P-wave peak is identified, and the average time at which the turning point appears, relative to the R-wave peak, is selected as point 320.

The steps taken in FIG. 6 to identify an "intrinsic" P-R interval are optional. Some examples may use the intrinsic P-R interval as determined in FIG. 6 to select a desired P-wave to Pace interval. For example, the P-wave to Pace interval may be calculated as a fraction of the P-R interval such as 30% to 70% thereof, or more or less. It may be that for an individual patient the desired fraction may be different due to patient-specific physiology. The method of FIG. 6 may be performed one time at implant, selectively at clinical follow-ups, or more frequently during ambulatory operation such as once a day when the patient is determined to be inactive, with adjustments to the desired P-wave to pace interval as needed.

In other examples the P-R interval may not be relied upon to determine the desired P-wave to Pace interval. For example, simply testing using feedback by, for example, delivering pace pulses at various P-wave to Pace intervals until fusion is observed, may allow the desired P-wave to Pace interval for a given patient to be set. In other examples, an assumption may be made as to a desired P-wave to Pace interval using a set value or a formula, at least initially, and adjustments may be made according to whether the patient responds well to therapy. For example, the P-wave to Pace interval may be a fixed duration such as 120 milliseconds, or a duration in the range of about 100 to 150 milliseconds, or some other value. The P-wave to Pace interval may also take the form of a fixed duration (such as 120 milliseconds), plus or minus some factor to account for the patient's intrinsic cardiac rate. A physician may be allowed to select a desired P-wave to Pace interval based on that physician's knowledge of the patient in some examples.

Figure 7:
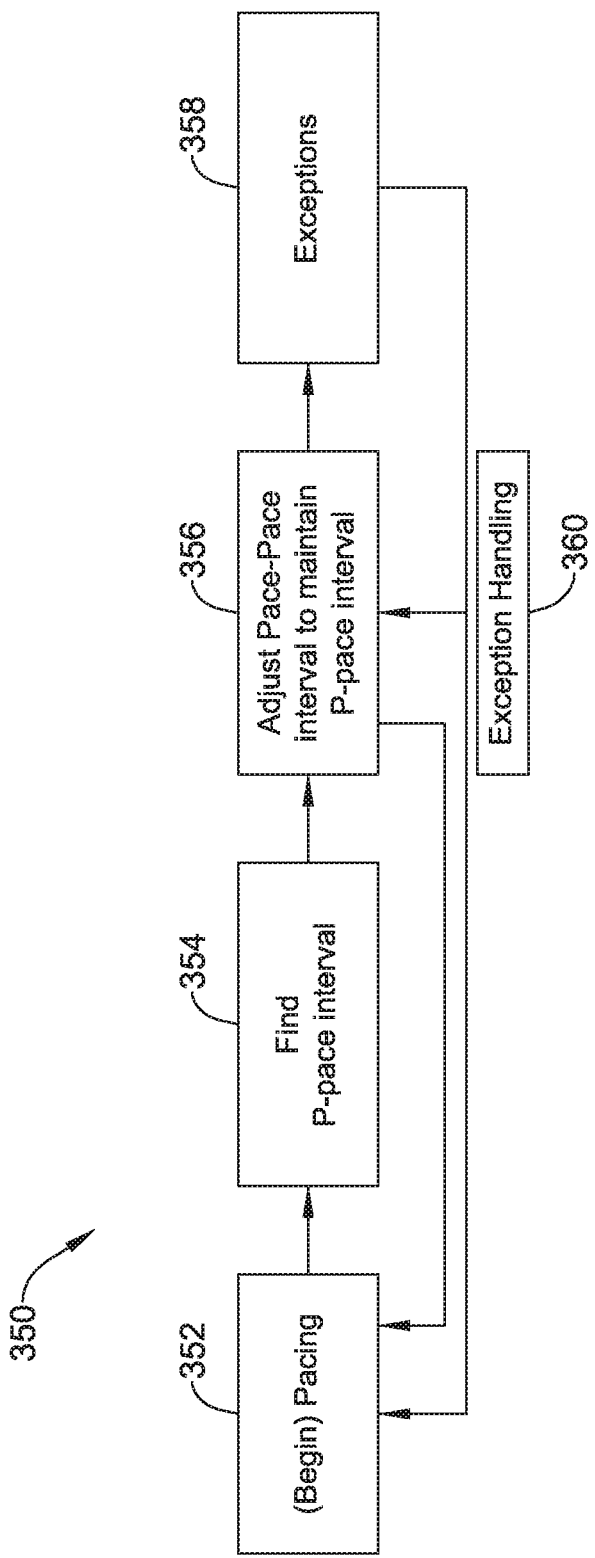
FIG. 7 shows an illustrative method of operation for a multiple device CRT system.

FIG. 7 shows an illustrative method 350 of operation for a multiple device CRT system. At block 352, the system begins pacing. In an example, an LCP, which may be implanted in or on the left ventricle, begins delivering pace therapy as shown below in FIG. 8. Next, the system finds a P-wave to Pace interval, as shown at 354. For example, the P-wave to Pace interval may be found by an extracardiac device such as an SICD or SCM, analyzing a signal it senses (which may contain both the pace signal and the P-wave), or by combining data from a sensed signal with data obtained from an LCP (such as timing data for a pace delivered by the LCP). The LCP may determine the P-wave to Pace interval instead by receiving data from an extracardiac device telling it when the P-wave was sensed.

Next, using the P-wave to pace interval from block 354, the system determines whether to adjust the Pace to Pace interval used by the LCP, in order to maintain a target P-wave to Pace interval. For example, the extracardiac device may calculate the P-wave to Pace interval and compare to a target, and then communicates to the LCP. Such communication to the LCP in block 356 may take the form of suggested, requested, or commanded adjustments to an LCP. Alternatively, the extracardiac device may calculate an interval and communicate the interval to the LCP, as may be useful if a wearable device is used in combination with an LCP, where the LCP may store physician-generated or patient-obtained data or settings that the wearable device may not have access to.

In some examples, the LCP may receive a command to deliver a pace at a given interval that is calculated by the extracardiac device. For example, the extracardiac device may issue a command to deliver a pace at a given Pace-to-Pace interval, with the extracardiac device also performing steps to determine the resulting P-wave to Pace interval as discussed herein. Then, the extracardiac device can adjust its Pace to Pace interval to account for corrections to the P-wave to Pace interval. For such an example, the LCP may not track its own Pace-to-Pace intervals and instead operates as slave to the extracardiac master device. Thus block 356 would encompass the extracardiac device modifying a saved parameter, while pacing block 352 would be triggered by the extracardiac device issuing a communication upon expiration of a predetermined interval.

In some examples, an "ideal" or target P-wave to Pace interval may be calculated as a percentage of the intrinsic P-R interval, using a measured P-R interval as shown above in FIG. 6. Alternatively, a theoretical intrinsic P-R interval may be calculated using a formula based on an intrinsic R-R interval, with the intrinsic R-R interval determined by simply turning pacing off for a few beats (4 to 20 beats, for example, or more or less) to allow observation of the intrinsic rhythm (for non-pacemaker dependent patients, that is). In other examples, a target P-wave to Pace interval may be determined by observing the patient's actual cardiac contractions, as determined using, for example, blood pressure signals, or by analysis of the degree of fusion that is achieved with various P-wave to Pace intervals. For example, a testing phase may observe cardiac output while attempting pacing using a series of longer and shorter P-wave to Pace intervals. In another example, cardiac electrical signals may be analyzed as the P-wave to Pace interval is manipulated in order to determine whether and at what interval(s) fusion beats can be observed, as opposed to intrinsic beats (indicating a P-wave to Pace interval that is too long—that is, the Pace occurs too late to arrive concomitant with the intrinsic signal/beat) or LV paced beats (indicating a P-wave to Pace interval that is too short—that is, the Pace occurs too early to arrive concomitant with the intrinsic signal/beat).

Various exceptions may arise, as indicated at 358 and handled as indicated at 360. Some exceptions may include the identification of an arrhythmia such as a supraventricular arrhythmia (atrial fibrillation for example), that makes the calculation or use of P-wave to Pace intervals problematic, and/or the presence of a ventricular arrhythmia requiring, potentially, a different therapy intervention such as defibrillation or anti-tachycardia pacing in place of CRT. Exceptions may also arise if the P-wave signal drops to a low amplitude, or if the presence of noise (motion artifact or electromagnetic interference, for example) makes P-wave detection difficult or unreliable. Loss of P-wave may be handled as shown in FIG. 13, by retaining existing Pace to Pace parameters at least until a timeout, by revisiting vector selection as shown by FIG. 5 (or simply switching sense vector configuration). Another exception is the potential for a ventricular extra-systole, such as a premature ventricular contraction, which may be addressed as shown in FIG. 14.

Exception handling 360 may also respond to an exception 358 by interrupting or ceasing pacing for a period of time to observe intrinsic cardiac signal characteristics, to re-initialize one or more features, such as sense vector selection or other sensing configuration, or to determine intrinsic cardiac signal characteristics such as the P-R interval. In some examples, the system may periodically cease pacing; if desired such a step may be handled through the exception and exception handling blocks 358, 360.

Figure 8:
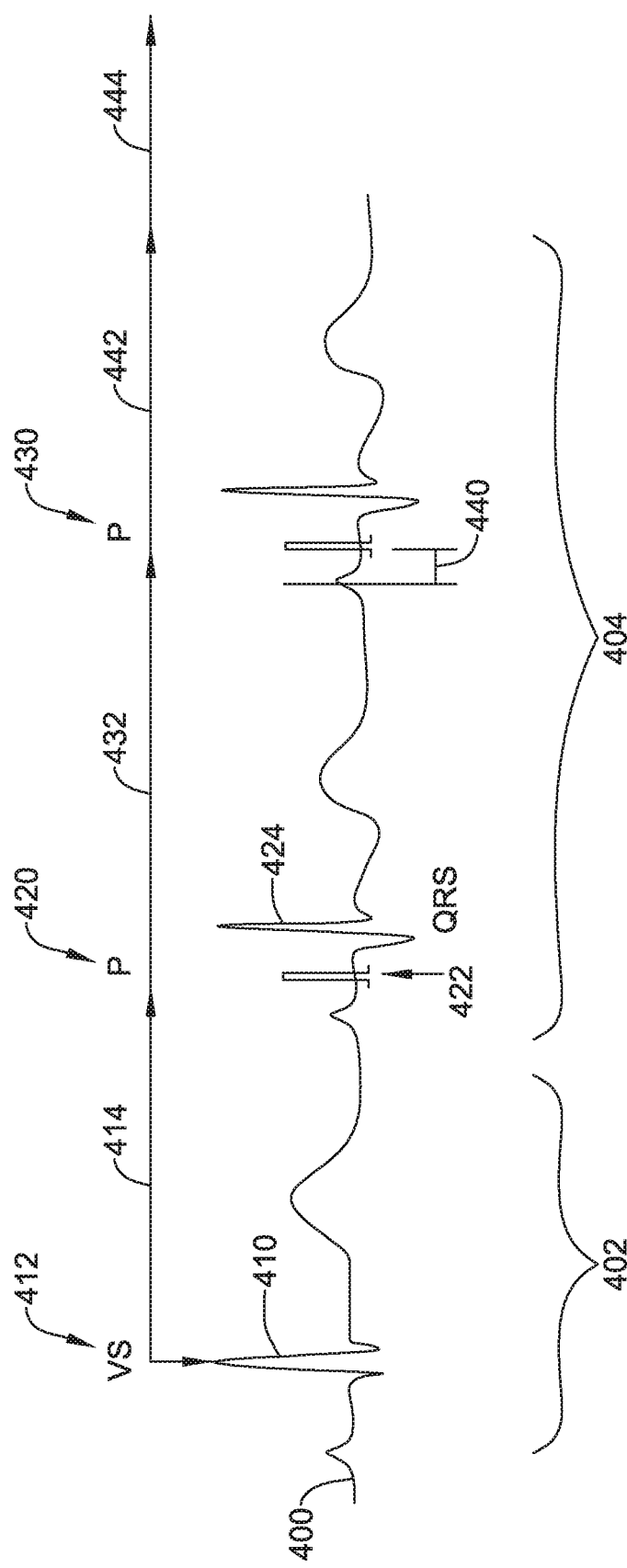
FIG. 8 illustrates, relative to a cardiac signal, a method of operation.

FIG. 8 illustrates, relative to a cardiac signal, a method of operation. A cardiac signal is shown at 400. A first cycle is highlighted at 402, with subsequent iterations at 404. A first pace pulse may be delivered according to first parameters for use in the first cycle 402, while subsequent iterations may use second parameters. In the illustration, a first cycle has a QRS complex shown at 410 and is detected as a ventricular sense 412 by either an LCP or an extracardiac device.

An interval 414 is defined to a first pace delivery 420, resulting in therapy delivery shown figuratively at 422. For simplicity the pace pulse 422 is shown as monophasic. It should be understood that any of monophasic, biphasic or other multiphasic pacing may be used, and the therapy output may be provided according to a constant, ramped or decaying, current-controlled or voltage-controlled waveform.

The pace pulse 422 is followed by a QRS complex at 424. A next pace therapy is delivered at 430 after expiration of a Pace to Pace interval 432. In illustrative examples, it is this interval 432 that can be dynamically modified to attain a desired P-wave to Peak interval. More particularly, while the LCP is delivering the pace 430, an extracardiac device is configured to capture the cardiac signal in a window preceding the pace 430 in order to calculate a P-wave to Pace interval 440. By setting a target value for the P-wave to Pace interval 440, it may be determined (by the LCP or by the extracardiac device) whether the Pace to Pace interval 432 is to be extended or shortened.

In some examples, the extracardiac device observes both the timing of the P-wave and the pace 430, and calculates interval 440. Alternatively, the extracardiac device may observe the timing of the P-wave and obtain data from the LCP indicating the time at which the pace 430 was delivered by reference, for example, to a synchronized clock. The interval itself may be communicated from the external cardiac device to the LCP which can then calculate an adjustment, if any, or an adjustment, if any, may be determined by the extracardiac device and communicated to the LCP. In other examples, the extracardiac device may observe the timing of the P-wave, and communicates to the LCP which, having delivered the pace 430 itself, can then determine the interval 440. In some examples, the extracardiac device may issue a command to deliver a pace, with the extracardiac device also performing steps to determine the resulting P-wave to Pace interval as discussed herein and then tracking and using pace commands to manage a Pace to Pace interval.

Figure 10:
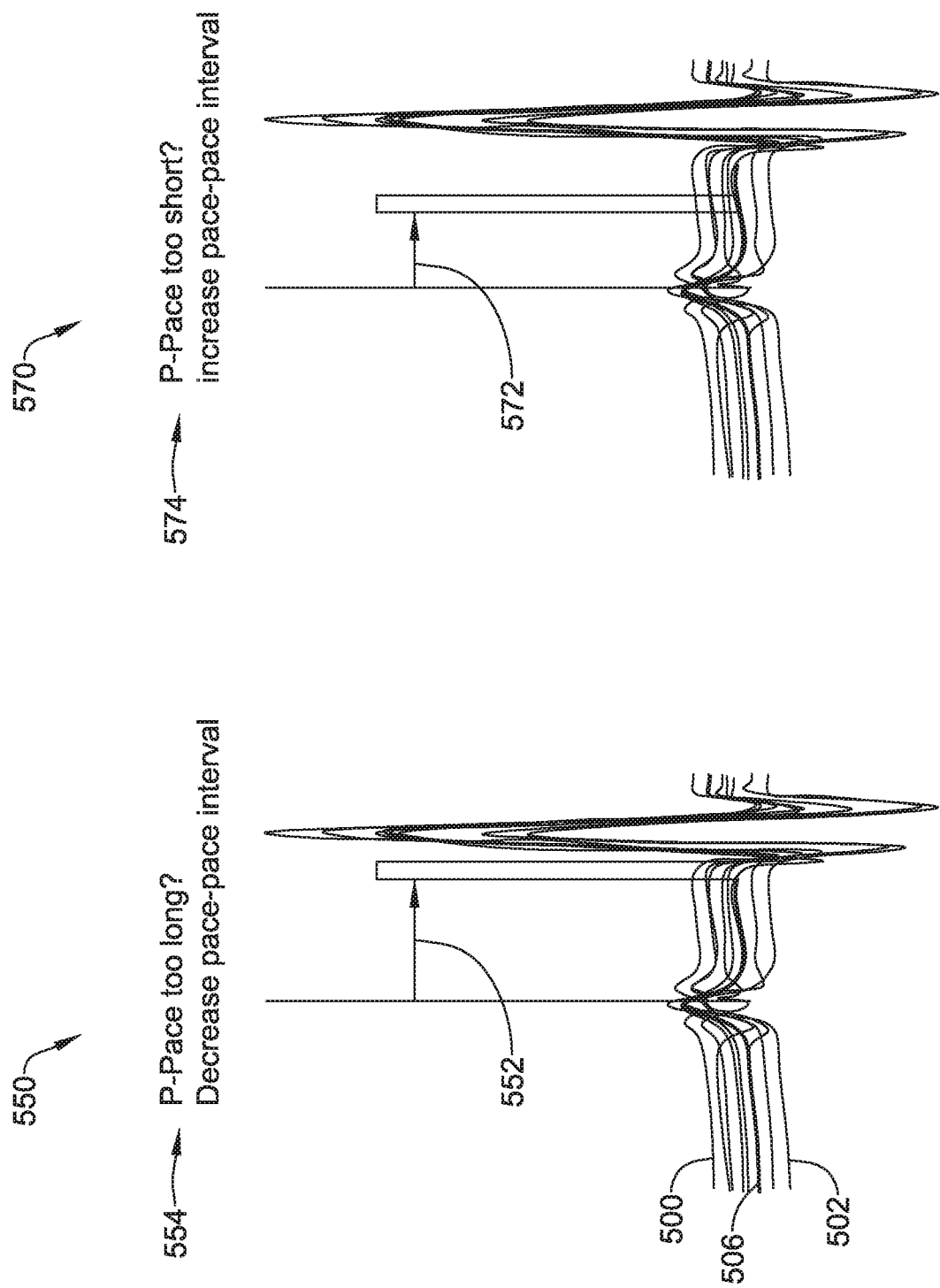
FIG. 10 illustrates, relative to a cardiac signal, analyses and modifications of Pace to Pace intervals.
Figure 11:
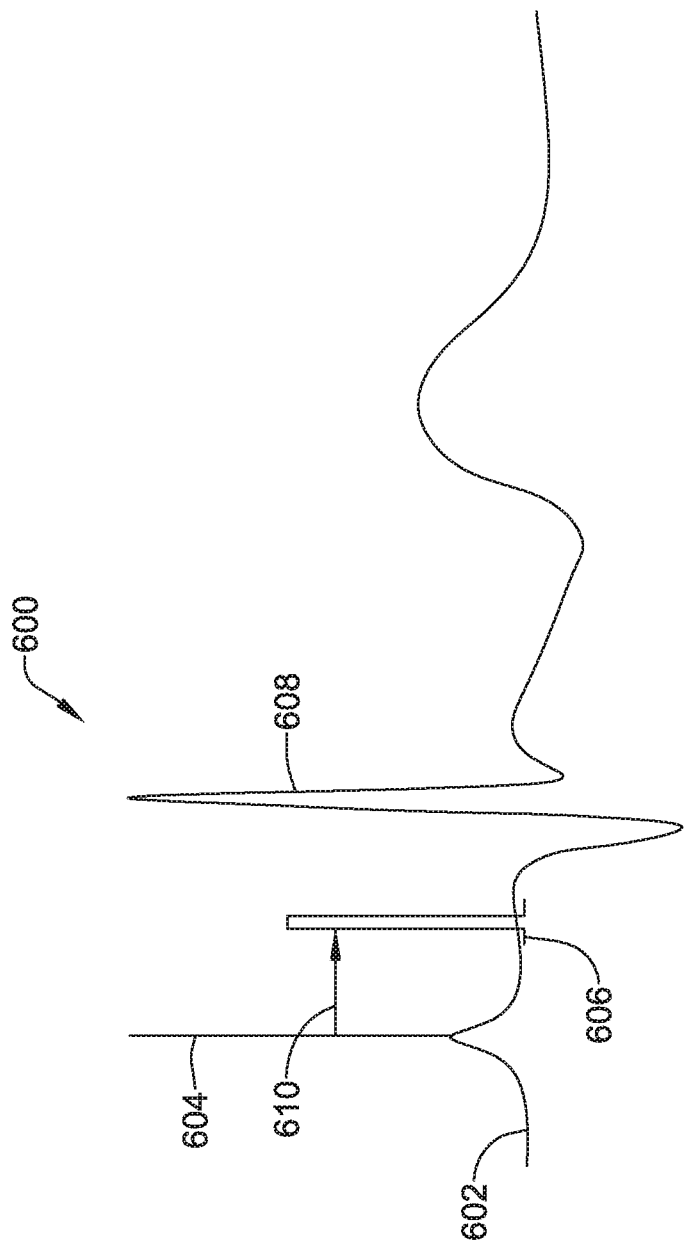
FIG. 11 illustrates another method of calculating P-wave to Pace interval.
Figure 12:
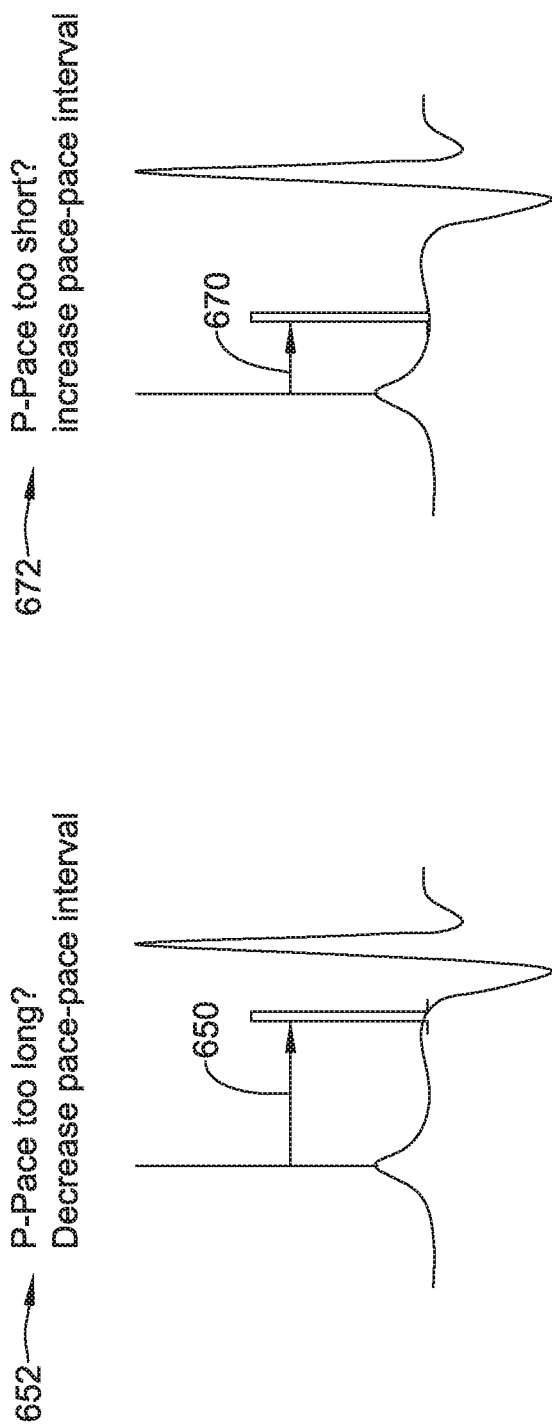
FIG. 12 illustrates, relative to a cardiac signal, analyses and modifications of Pace to Pace intervals.

In some examples, the Pace to Pace interval 442 that immediately follows pace 430 may be manipulated in light of the interval at 440. In other examples, due to system lag or design choice, it may be a next Pace to Pace interval 444 that is in fact manipulated in response to interval 440. In still further examples, a composite signal may be used to control or manage the Pace to Pace interval 444, such that updates occur periodically as the analysis of the composite signal is completed, for example, using methods illustrated below in FIGS. 9-10. Alternatively, adjustments may made on a beat to beat basis as shown by FIGS. 11-12.

In the illustration, the pace pulse 422 has caused a fusion beat in which the paced QRS complex 424 has quite different morphology characteristics than the intrinsic QRS complex at 410. If desired, fusion morphology analysis may be used to adjust the target value for the P-wave to Pace interval 440. For example, if morphology analysis shows that the QRS complexes associated with pace therapy delivered at a target P-wave to Pace interval fails to yield desirable characteristics, such as fusion, the target may be extended or shortened, if desired. For example, if the morphology shows beats resembling intrinsic beats, this may be addressed by delivering the pace therapy earlier and shortening the P-wave to Pace target interval. If the morphology shows beats resembling LV pace captured beats, this may be addressed by delivering the pace therapy later and extending the P-wave to Pace target interval.

Rather than using cardiac electrical signal morphology, other characteristics, such as patient functional measurements, heart sounds, blood pressure or other features, may be used to determine that a given P-wave to Pace target interval is not achieving a desirable outcome and that an adjustment is to be made. Some examples may use, for example, a sampled impedance signal that yields cardiac cycle information. Such analysis can be used to determine whether the target P-wave to Pace interval is achieving a desired goal such as the occurrence of fusion beats; if not, then the target P-wave to Pace interval can be adjusted by extending it (if LV pace morphology is observed) or shortening it (if intrinsic morphology is observed).

Figure 9:
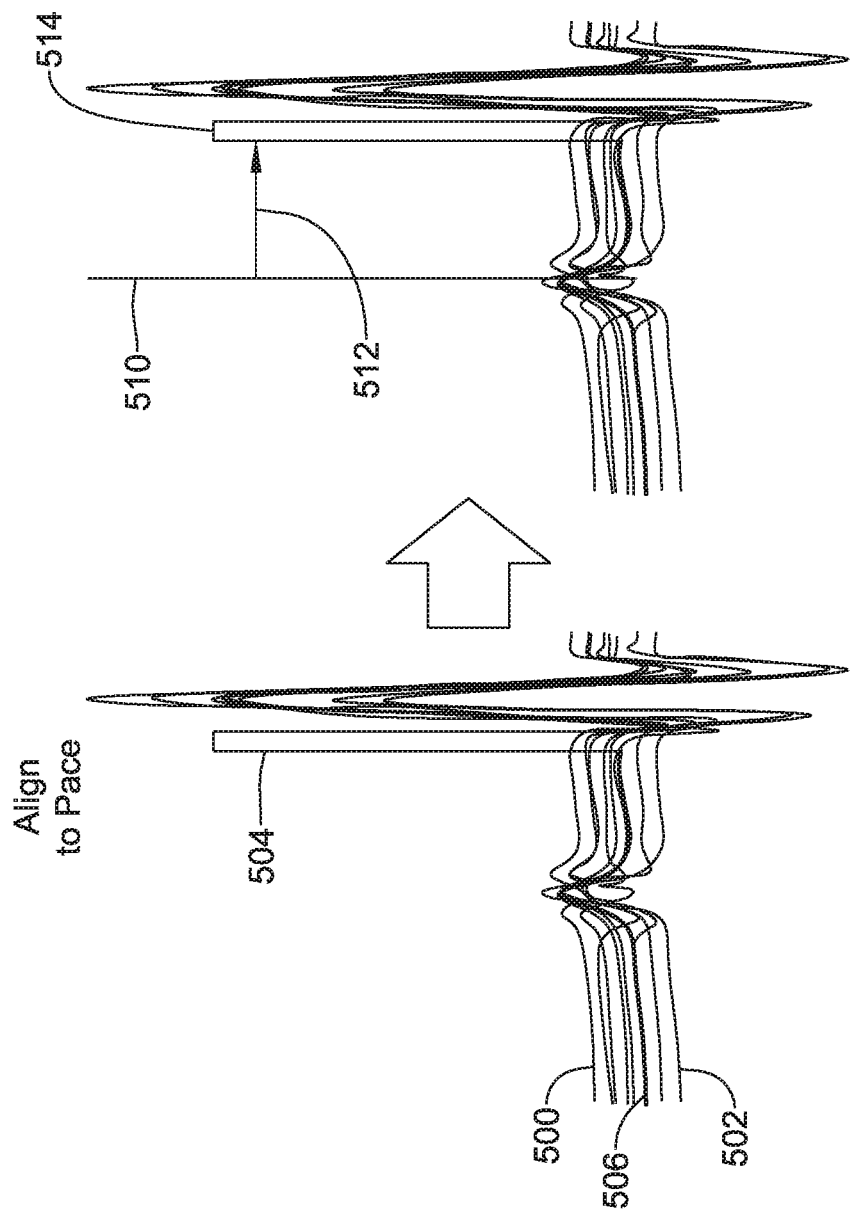
FIG. 9 illustrates a method of calculating P-wave to Pace interval.

FIG. 9 illustrates a method of calculating P-wave to Pace interval using a composite signal. A plurality of cardiac signals 500, 502 are combined together, using the pace therapy associated with each signal 504 as an alignment fiducial. The result is a composite signal 506. The composite signal 506 is then analyzed as shown at the right, with the P-wave peak identified at 510 and an interval 514 from the P-wave peak to the Pace therapy 514 is calculated, for use as shown in FIG. 10. Pulse timing in each of the signals may be determined by measurement of an extracardiac device (which may sense both the cardiac signal and the pace pulses 514), or by calculation of the timing of the pace pulse as communicated by an LCP to an extracardiac device. In some examples, if the LCP is performing the analysis, the extracardiac device may communicate timing data along with data for cardiac signals 500, 502 to allow the LCP to align the delivered pace pulse times (which the LCP would know) to individual cardiac signals 500, 502.

FIG. 10 illustrates, relative to a cardiac signal, analyses and modifications of Pace to Pace intervals. A first analysis and response is shown at 550. Here, the P-wave to Pace interval 552 is longer than the target. For example, when the patient's intrinsic sinus rate begins to change the prior Pace to Pace interval ceases to be as effective as it would have been prior to changes in the intrinsic rate. Thus, for example, the Pace comes late after the atrial event because the atrial event occurs earlier in the cycle as sinus rate increases. The illustrative system will retrospectively identify the change in P-wave to Pace interval, and corrects the Pace to Pace interval in response.

As indicated at 554, the rule determines whether the P-wave to Pace interval is too long—that is, longer than a target, or longer than a target by a threshold amount, for example. If so, the pace-pace interval is made shorter, which would in turn reduce the length of interval 552. For example, if interval 552 is too long, this may put the pace therapy closer to the QRS onset than desired. The resulting cardiac cycle may resemble the patient's intrinsic cardiac beat, and the LV (for an LV placed LCP) may fail to contract artificially early in the cardiac cycle to produce desired fusion and improved cardiac function. Adjustments may occur at a fixed step size or may be performed in larger or smaller increments based on the observed P-wave to Pace interval to attempt immediate correction in one step.

A second analysis and response are shown at 570. Here, the P-wave to Pace interval 572 is shorter than the target. This may occur if the patient's sinus rate drops upon cessation of activity such as walking, or possibly if the patient has gone to sleep. Because the atrial event occurs later in the cycle, the pace therapy occurs closer to the P-wave than is desired, and the illustrative system is configured to retrospectively identify this change and respond to it.

As indicated at 574, the rule determines whether the P-wave to Pace interval is too short—that is, shorter than a target, or shorter than a target by a predetermined amount, for example. If so, the pace-pace interval is made longer, which in turn would increase the length of interval 572. For example, if interval 572 is too short, this may put the pace therapy farther from the QRS onset than desired. The resulting cardiac cycle may resemble an LV captured beat (for an LV placed LCP), with the LV contracting too early in response to the pace pulse and failing to produce desired fusion and improved cardiac function.

Thus FIG. 10 demonstrates how changes in the patients underlying heart (sinus) rate may be followed/adjusted "retrospectively" by measuring the p-pace interval and then adjusting the pace-pace interval accordingly to "follow" the sinus rate.

When using a composite signal as shown in FIGS. 9-10, the composite signal may be updated on a beat to beat basis, or may be updated at intervals, for purpose of re-running the analysis of the P-wave to Pace interval. For example, analysis may take place at intervals of four to one-hundred seconds, or more or less. Rather than fixed time period, the analysis may take place once every four to one-hundred cardiac cycles, or more or less cycles, as desired. The quantity of signal waveforms may be varied as well, using anywhere from four to over a hundred cardiac cycle signals. It may be desirable to avoid overcomplication (and excessive calculations and power draw) by using a quantity in the range of about 4 to about 24 signals, though more may be used as desired.

In an alternative example, a tiered approach may be used for the updating. For example, the default mode may run the analysis at a first interval as long as neither of the adjustments at 550, 570 are needed; if adjustments are needed, or if operating after a pause in pacing, for example, a second, shorter interval may be used. For example, the P-pace interval may be checked once a minute as a first interval, and, when adjustments are made, a shorter, ten second interval may be used between re-analyses. In one embodiment, a quantity of cardiac cycles, rather than passage of time, is used. For example, analysis may occur every sixteen cardiac cycles except at initiation of pacing or when adjustments or exceptions arise, during which analysis may occur every four or eight cardiac cycles. These numerical examples are provided for illustration and are not intended to limit the invention.

FIG. 11 illustrates another method of calculating P-wave to Pace interval. The graphic 600 shows a cardiac signal 602 through approximately one complete cycle. The P-wave peak is flagged at 604 by, for example, searching for a P-wave window (as discussed in U.S. Provisional Patent Application Ser. No. 62/355,121) and/or by applying a threshold to the cardiac signal following the end of a preceding T-wave, or by searching a time period prior to the delivered pace pulse 606 and/or R-wave or QRS complex 608.

A P-wave to pulse interval 610 can then be measured or calculated. For example, an extracardiac device may detect both the cardiac signal as well as the pace pulse delivery by an LCP and perform analysis as shown. Alternatively, the extracardiac device may receive timing information for the pace pulse by communication from an LCP, and align the pace pulse to the cardiac signal. In still another example, if the LCP is performing the analysis, the extracardiac device may communicate timing data along with data for cardiac signal 602 to allow the LCP to align the delivered pace pulse times (which the LCP would know) to the signal 602.

The interval 610 found in FIG. 11 can then be used as shown in FIG. 12, which illustrates, relative to a cardiac signal, analyses and modifications of Pace to Pace intervals. The analysis is similar to that of FIG. 10. If the interval 650 from P-wave to pace is too long, then the Pace to Pace interval can be reduced as indicated at 652. On the other hand, if the interval 670 from P-wave to Pace is too short, then the Pace to Pace interval is extended, as indicated at 672. The determination of short and long may be made relative to a single target value, or may be relative to thresholds or boundaries around a target value, as desired.

In one manner of explaining several of the above examples, the LCP may operate in a VVI pacing mode (a pacemaker in VVI mode denotes that it paces and senses the ventricle and is inhibited by a sensed ventricular event). Rate adjustments are made to the LCP VVI rate using ancillary information from the extracardiac device, with the ancillary information related to the timing of the P-wave relative to the ventricular pace. Optimization at a fixed sinus rate could be readily achieved and the VVI rate (defined by the Pace to Pace interval) would stay stable if the sinus rate never changed. However, because the sinus rate changes, there is a need for adjustment to keep the desired P-wave to Pace interval in effect. Adjustments to the Pace to Pace interval may occur frequently if the sinus rate is changing, and may be infrequent if the sinus rate is stable.

FIGS. 13-14 show illustrative exception handling methods in graphic form. FIG. 13 shows a first example at 700. The cardiac signal is shown, as sensed by an extracardiac device, at 702. A pace pulse is delivered at 704 and analysis may be done as shown above (FIGS. 9-12, for example) to assess, retrospectively, the timing of the pace pulse 704 relative to the P-wave 706 preceding the QRS complex 708. If needed, one or more subsequent Pace to Pace intervals (714 and/or 724) may be adjusted based on assessment of the P-wave to Pace interval.

However, in the next cardiac cycle, the P-wave has dropped out, as shown at 710, which illustrates that the P-wave is not found in the time period preceding pace pulse 712. This creates an exception insofar as the P-wave to Pace interval cannot be calculated or analyzed. In the example shown, the exception handles this situation by preserving the most recently calculated (and/or adjusted) Pace to Pace interval. Thus, if analysis of the P-wave to Pace interval at 706 to 704 is used to adjust interval 714, then intervals 724 and 734 would preserve the value of the last calculated Pace-Pace interval 714. If analysis of the P-wave to Pace interval at 706 to 704 is used to adjust interval 724 (relative to interval 714, as needed), then interval 734 would preserve the value of interval 724.

In the example shown, the P-wave continues to be absent at 720, relative to pace 722, and again at 730, relative to pace 732. Thus the preservation of existing values may go on for several additional cardiac cycles. In some examples, a maximum "carry" forward time or quantity of cardiac cycles may be defined. For example, absent a P-wave for 30 seconds (or in the range of about 5 to about 120 seconds, or more or less), the system times out and ceases pacing using the P-wave to Pace interval. In another example, if 30 pace pulses are delivered (or in the range of about 5 to about 120 pace pulses, or more or less) without a P-wave, the system may time out and cease pacing using the P-wave to Pace interval as a guide for determining pacing intervals.

FIG. 14 illustrates another exception handling method. The cardiac signal as observed by the extracardiac device is shown at 750. A first pacing pulse is delivered at 754, causing a fusion beat represented at QRS complex 756. The P-wave is present as shown at 752, though it need not be for this exception case, which may operate as an exception within another exception.

On expiration of the Pace to Pace interval 760, another pace pulse is delivered at ix) 758. Here, the P-wave is barely discernible; this may trigger the exception case of FIG. 13. Following QRS complex 762, a ventricular extra-systole occurs in the form of a premature ventricular contraction (PVC) 770. The Pace to Pace interval 774 has not yet expired, however, the pace pulse that would occur at 772 is shown in phantom, indicating it is not delivered. For example, an LCP may sense the PVC 770 and withhold pacing pulse 772. Alternatively, an extracardiac device may also sense the PVC and issue a communication calling for inhibition of the pace pulse 772.

Thus pace pulse 772 is withheld in response to the PVC 772. In this exception rule, the system simply restarts the Pace to Pace interval and, upon expiration of interval 776, a next pace pulse is delivered at 778. The pace delivery at 778 thus takes place at an interval that is double the Pace to Pace interval currently in effect; system values are otherwise preserved in this example.

Figure 15:
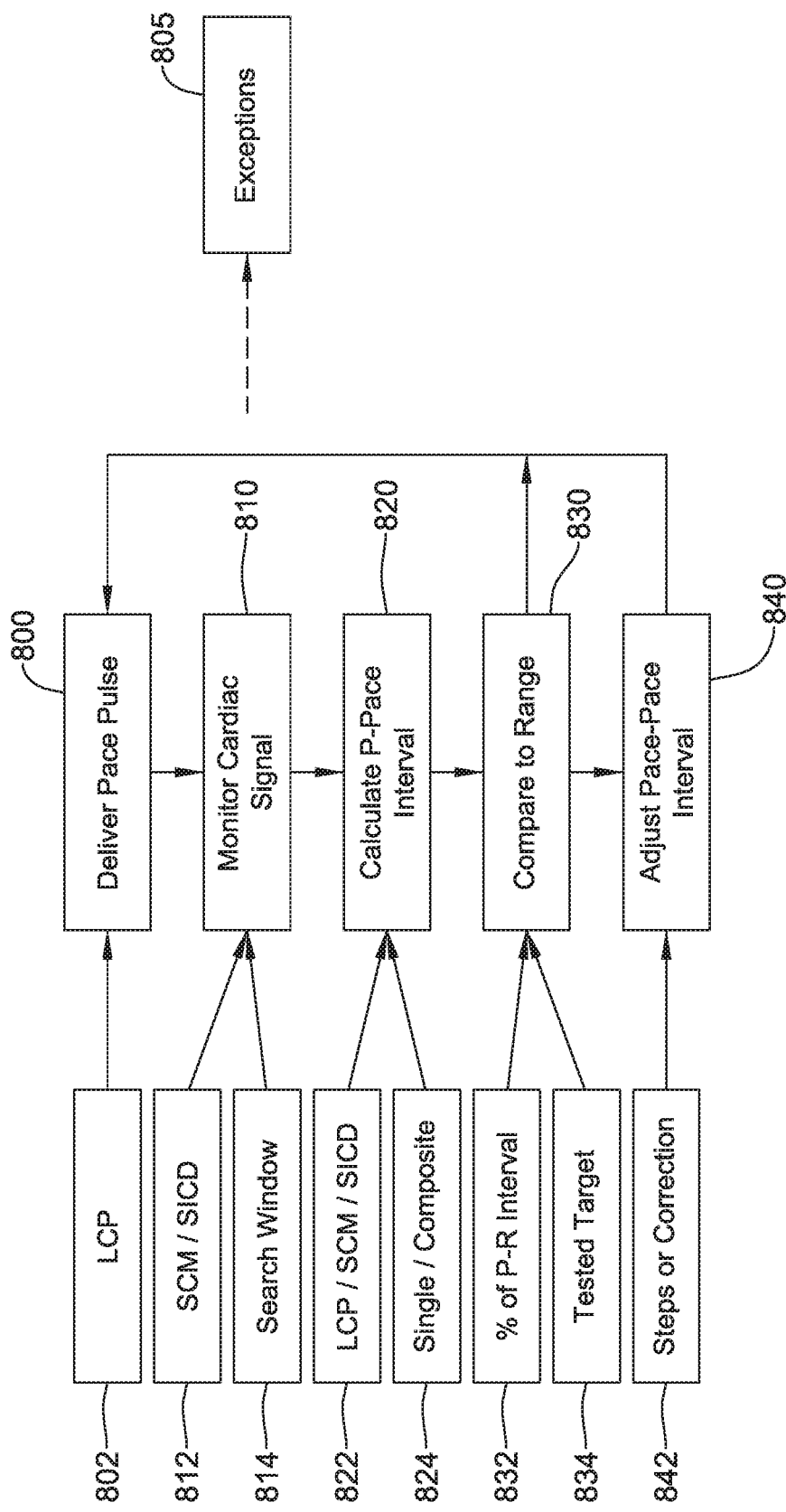
FIGS. 15-18 show illustrative methods and/or devices.

FIGS. 15-18 show illustrative methods and/or devices. FIG. 15 shows in block form an illustrative method, including steps of delivering one or more pace pulses at 800, monitoring a cardiac signal at 810, calculating a P-wave to Pace interval at 820, comparing the calculated P-wave to Pace interval to a desired range at 830, and, as needed, adjusting a Pace-to-Pace interval as shown at 840 for use as the method iterates back to block 810. Exceptions may occur as indicated at 805, such as if the P-wave cannot be identified, if a PVC occurs, or an arrhythmia is identified, as noted above in FIGS. 13-14.

Within the overall method, various steps may have further details and options. The delivery of the pacing pulse 800 may take place with the pace therapy delivered by a leadless cardiac pacemaker as indicated at 802. As noted above, the LCP may track the pace to pace interval and make adjustments as requested, suggested, or based on information provided by the extracardiac device. In some examples, the LCP 802 may deliver a commanded pace at block 800, with the extracardiac device managing Pace to Pace intervals and using commands for pacing at appropriate times to effect a desired Pace to Pace interval.

Monitoring of the cardiac signal 810 may be performed, for example, by a subcutaneous cardiac monitor (SCM) or a subcutaneous implantable defibrillator (SICD), as indicated at 812. The monitoring may take place across a broad period of time such as the entire cardiac cycle, or a period of time unrelated to cardiac cycles, or may instead take place within a search window as indicated at 814. A search window 814 may be defined, for example, as a period of time preceding pace therapy delivery, if the pace pulse timing is known to the SCM or SICD, such as a window of 40 to 400 milliseconds, or more or less, preceding the pace pulse delivery. Alternatively, a search window 814 may be defined relative to a detected R-wave, using for example a window within a range of about 60 to about 500 milliseconds prior to the detected R-wave.

The calculation of a P-wave to Pace interval 820 may be performed by any of the different devices within a system in various cooperative or independent modes, as indicated at 822. For example, the LCP and SCM or SICD may cooperate by having the LCP communicate a time at which a pace pulse was delivered to the SCM or SICD, with the SCM or SICD calculating when the P-wave occurred relative to the pace pulse and then calculating the interval. In another example, the LCP and SCM or SICD may cooperate by having the SCM or SICD communicate a time at which the P-wave occurred to the LCP, with the LCP having recorded the time at which it delivered a pace pulse, such that the LCP can then calculate the interval. In a non-cooperative example, an SICD or SCM may sense both the delivery of a pace pulse and the P-wave, and can then calculate the interval without needing a communication to or from the LCP. In some examples, as indicated at 824, the P-wave to Pace interval may be calculated using data for a single cardiac cycle (see FIGS. 11-12); in other examples, the P-wave to Pace interval may be calculated using a composite signal (see FIGS. 9-10).

The comparison to a range 830 may include using a range set as a percentage of the P-R interval, such as by using a method as in FIG. 6 (or alternatively using a single cardiac cycle analysis to find the P-R interval), as indicated at 832. In other examples, the range can be set by using a tested target, as indicated at 834, by delivering pacing pulses at various P-Pace intervals to determine an interval for a given patient that yields desirable results such as cardiac fusion. The desirable results may be determined using an electrical signal (finding, for example, a fusion beat has taken place as opposed to an intrinsic beat or an LV capture beat using features of the cardiac electrical signal), or using other measures such as through analysis of blood pressure, pulse oxygenation, heart sounds, impedance, or patient functional abilities, or other physiological response.

Adjustments can be made to the Pace-Pace interval as indicated at 840 by using a stepwise change to the Pace-Pace interval, or by simply making a correction, as indicated at 842. A step-wise change may, for example, increase the Pace-Pace interval in predefined steps of about 20 to about 50 milliseconds, or smaller or larger steps. A correction may, for example, determine how far away from the P-wave to Pace interval range or target a measurement is, and applies a correction matching the identified discrepancy.

In some examples, if the P-Pace interval found at 820 is in range at 830, the process may simply return to 800 without making an adjustment, omitting block 840 when in-range. In other examples, the Pace-Pace interval may be continuously varied even as the P-Pace interval is within the desired range.

Figure 16:
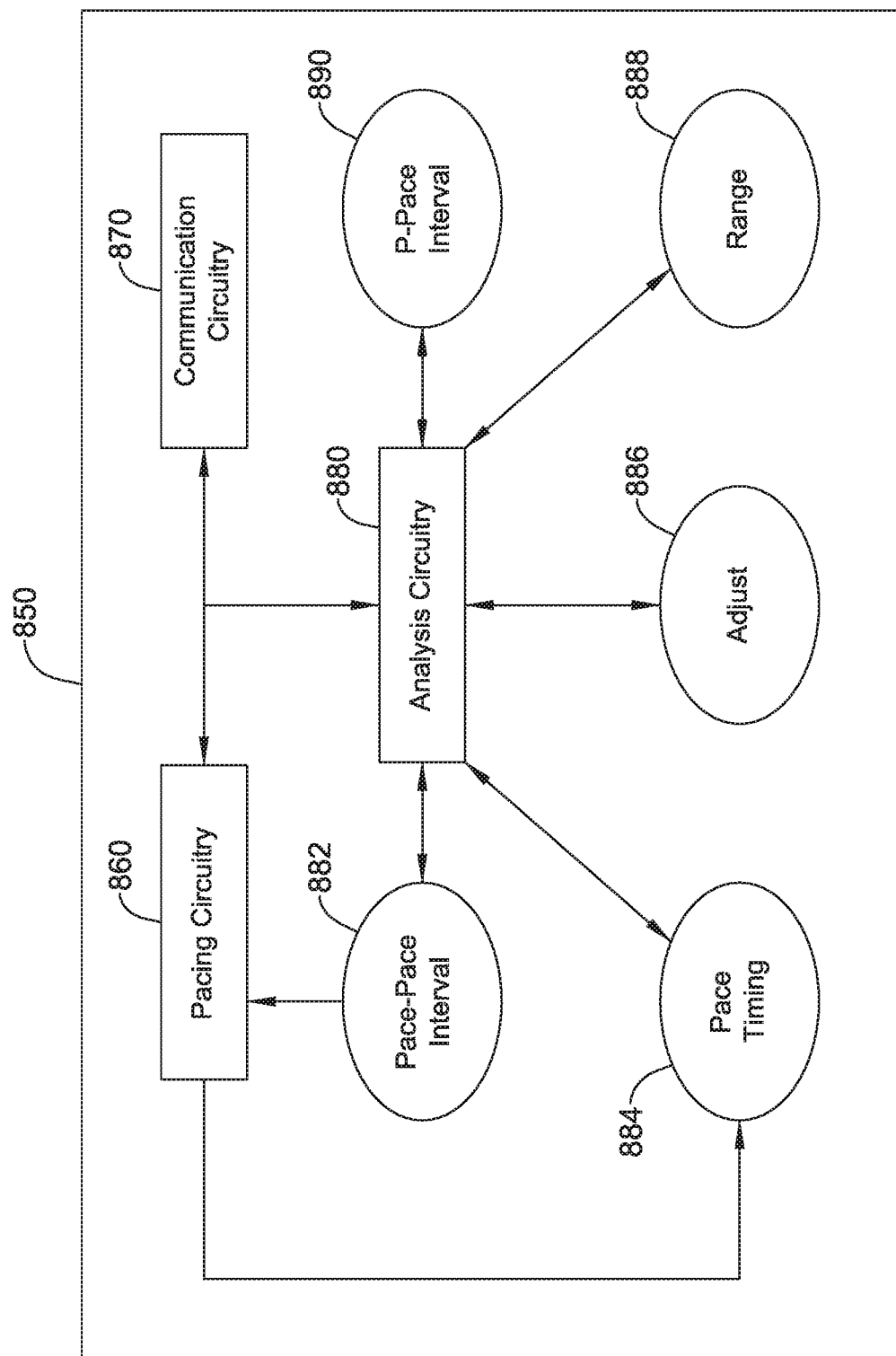

FIG. 16 is a block diagram for an illustrative device. The device 850 may take the form of an implantable leadless cardiac pacemaker (LCP) suited for implantation in a heart chamber of a patient, such as in the left ventricle; other cardiac locations (right ventricle or atria, for example, may be used instead). The device 850 is shown here with functional blocks of operational circuitry including pacing circuitry 860, communication circuitry 870, and analysis circuitry 880.

The pacing circuitry 860 can include output switches to control the start and end of output current or voltage flow, as well as suitable coupling capacitors to manage DC or other currents and biasing, and controls for managing, for example, the quantity of current and/or amount of voltage to be delivered. The communication circuitry 870 may include a transceiver circuit, antenna(s), coils or the like for use in RF or inductive telemetry. The communication circuitry 870 may also include control circuitry for managing conducted communication, such as sample and hold or analog to digital conversion circuitry to discern the content of conducted communications to generate digital data therefrom.

The analysis circuitry 880 may include a microcontroller and/or application specific integrated circuit to implement control circuitry, which may include a state machine, for controlling operations in the device 850. The analysis circuitry 860 may include modules, such as dedicated hardware or machine implementable instruction sets and memory to store relevant data or instructions for a variety of operations include various items shown, such as management of the pace-to-pace interval 882, recording the timing of pace delivery 884, adjustment calculations 886 for when the P-wave to pace interval (which can be calculated according to module or function 890) is outside a desired range (which range may be stored or managed according to module or function 888).

In an example, the analysis circuitry 880 is allowed to "sleep" by having the pacing circuitry 860 deliver pacing pulses according to the pace-pace interval 882 that can be accessed or used to control pacing circuitry 860 without needing action by the analysis circuitry 880, with the pace timing function 884 recording when pacing outputs are generated by the pacing circuitry 860. As needed or called, the analysis circuitry can use the pace timing from 884 to compare to P-wave timing information received via the communication circuitry 870 to identify the P-wave to Pace interval 890. The P-wave to Pace interval 890 can be compared to the desired range 888 by the analysis circuitry to determine whether an adjustment is needed at 886, with the analysis circuitry 880 then modifying the pace-pace interval 882 for implementation by the pacing circuitry 860. Other architectures may be used instead.

One alternative architecture may omit items 888 and 890, with the analysis circuitry 880 operating to communicate data related to pace timing 884 out viva the communication circuitry 870. Such outward communication may also occur without analysis circuitry 880 intervention, if desired, by having the communication circuitry 870 issue a pace timing communication in response to prompting by the pace timing circuitry 884 when a pace therapy is delivered. In another example, the communication circuitry 870 may poll the pace timing circuitry 884 and issue communication out when the pace timing circuitry 884 responds with a time of pace therapy output. The communication circuitry 870 may then listen for a respond from a second device, such as an SICD or SCM, indicating a calculated P-wave to Pace interval (determined by the second device) is out of range, causing the analysis circuitry 880 to activate and use the adjustment parameters 886 to determine a new pace-pace interval 882.

In a still further alternative, block 886 may also be omitted, and the communication from a second device may define a new Pace-Pace interval 882 that the analysis circuitry 880 implements. In a still further example, the communication circuitry 870, on receiving a message commanding a new Pace-Pace Interval be implemented, simply implements the pace-pace interval directly to block 882, bypassing the analysis circuitry 880 which may remain "asleep" until wake-up occurs in response to a wakeup command from the communication circuitry, until an exception (FIGS. 13-14, above, for example) is identified, or until some other reason for wakeup occurs.

Figure 17:
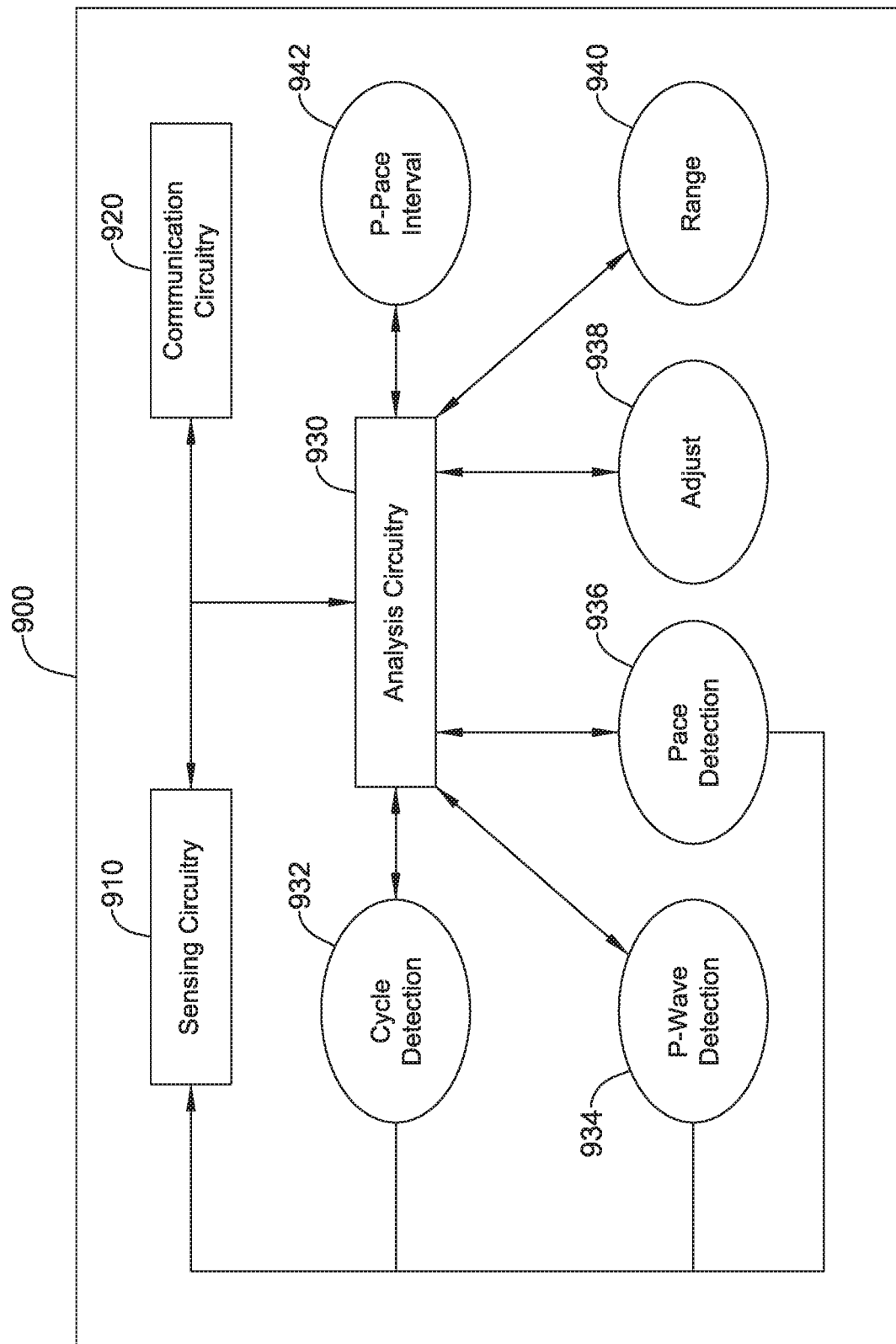

FIG. 17 shows another illustrative device in block diagram form. Here, the device 900 may be, for example, a subcutaneous implantable defibrillator (SICD) or subcutaneous monitor (SCM). The device 900 may, in an alternative, be a wearable device.

The device 900 comprises sensing circuitry 910, which may be coupled to electrodes (not shown, but see FIGS. 1-2, above). Also included is communication circuitry 920 and analysis circuitry 930. The communication circuitry 920 may include a transceiver circuit, antenna(s), coils or the like for use in RF or inductive telemetry. The communication circuitry 920 may also include control circuitry for managing conducted communication, such as sample and hold or analog to digital conversion circuitry to discern the content of conducted communications to generate digital data therefrom.

The analysis circuitry 930 may include a microcontroller and/or application specific integrated circuit to implement control circuitry, which may include a state machine, for controlling operations in the device 900. The analysis circuitry 930 may include modules, such as dedicated hardware or machine implementable instruction sets and memory to store relevant data or instructions for a variety of operations include various items shown. There may be dedicated hardware or instruction sets stored in memory to perform cardiac cycle detection 932, P-wave detection 934, which may, if desired, use a P-wave detection window, and/or pace detection 936. The analysis circuitry 930 may also access dedicated hardware or instruction sets or memory having parameters useful for the determination of what adjustments 938 may be needed, a desired range 940, and for calculation of the P-wave to Pace interval 942.

In an example, the sensing circuitry 910 performs steps related to cycle detection largely in hardware without requiring intervention by the analysis circuitry 930, though this is optional. P-wave detection 934 and pace detection 936 may also be hardware driven, to allow the analysis circuitry to have reported to it the occurrence of a cardiac cycle (from 932), the time at which a P-wave is identified in the cardiac cycle (from 934), and the time at which a pace therapy is detected in the cardiac cycle (from 936). The timing information for the P-wave and Pace can be used to calculate the P-wave to Pace interval as indicated at 942, which the analysis circuitry can then compare to the desirable range 940 and determine what, if any, adjustments to make at 938. The outcome can be an adjustment, as needed, to the Pace to Pace interval used by the pacemaker, which may be an LCP such as that shown in FIG. 16 and/or FIGS. 1 and 3, which can then be communicated out by the communication circuitry 920.

In an alternative, the adjustment block 938 is omitted, and the analysis circuitry may communicate an indication that the P-Pace interval is out of the desired range 940 and, preferably for this alternative example, at least the direction of the out of range status and/or the amount out of range. In a further example, the range function 940 is omitted as well, and the device 900 may communicate out a measurement of the P-wave to Pace interval. In a still further example, the P-Pace interval block 942 and (optionally) the pace detection block 936 may be omitted and the device communicates the timing of the P-wave only, allowing the LCP to do the rest of the analysis itself. In yet another example, the Pace detection circuit 936 can be omitted, and the analysis circuitry 930, or the P-Pace interval block 942, may obtain pace timing information from the pacemaker via the communication circuitry 920.

In some examples, some operations may take place without the analysis circuitry "waking" up from a low power or sleep state. As noted, blocks 932, 934 and 936 may be largely hardware driven to operate cooperatively with the sensing circuitry to derive the noted information from the cardiac signal. In another example, if the communication out is simply the time at which the P-wave is observed, the communication circuitry 920 may respond to or poll the P-wave detection circuitry itself. In another example, P-wave detection 934 and Pace detection 936 may be hardware driven, making calculation of the P-pace interval 942 a simple calculation that may also be driven in hardware with comparison to the range 940 also feasible in hardware, allowing the communication circuitry 920 to issue a communication of the P-wave to Pace interval, or whether that interval is in or out of the range 940, without intervention by the analysis circuitry 930.

Figure 18:
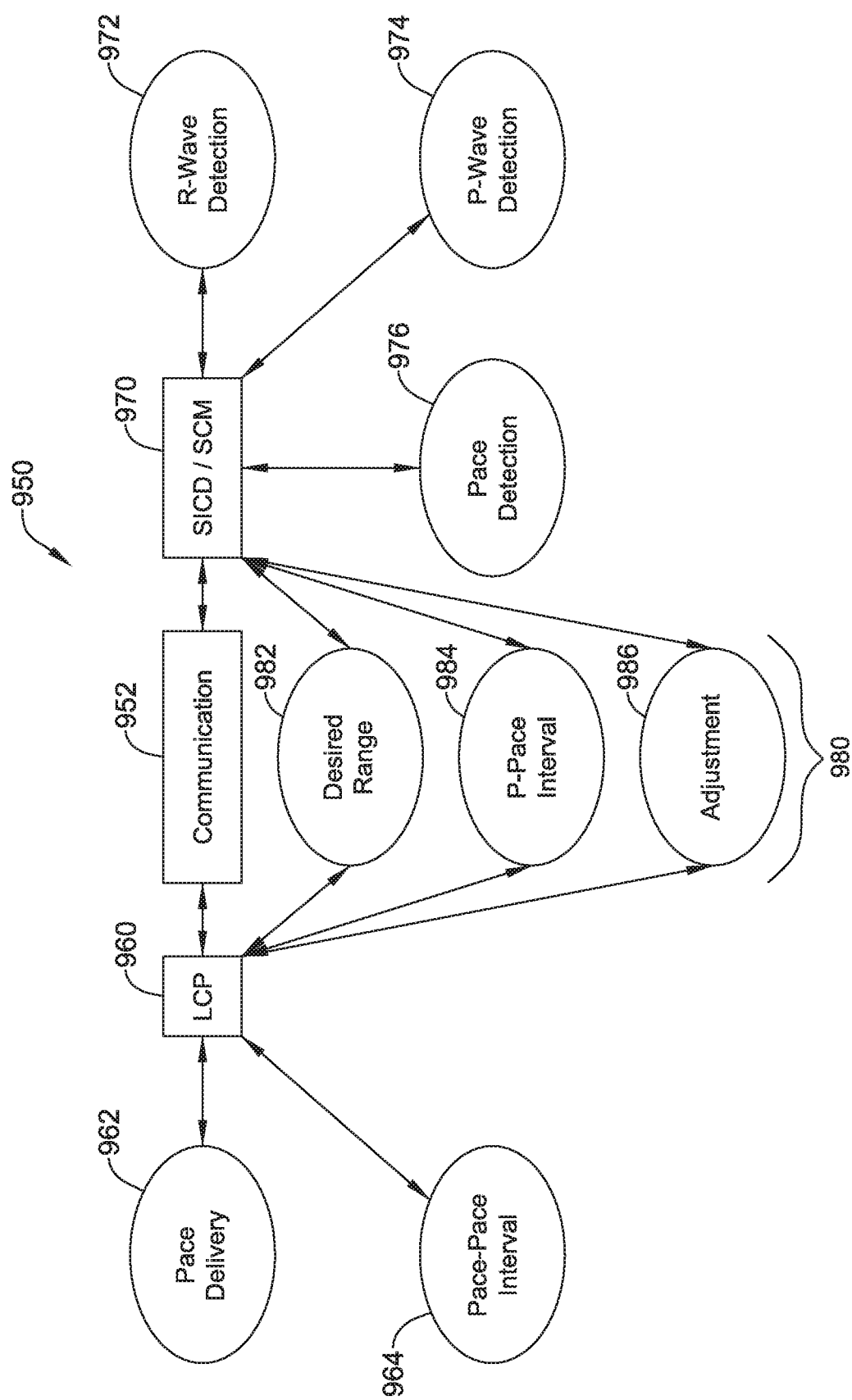

FIG. 18 illustrates a system level example with various functions allocated to different components. The system 950 includes an LCP 960 and SICD or SCM (an "extracardiac device" or ED) 970 that are configured to communicate 952 with one another via conducted communication or via some other modality such as inductive, optical, sonic, or RF communication. ED 970 may also be wearable. Some operations may be dedicated to one device or the other, or shared across the system in several examples.

For example, the LCP 960 will perform the pace delivery 962, and tracks a pace to pace interval 964 to control pacing therapy output. The ED 970 may include R-wave detection 972, though this is not necessary to the pacing control methods in several examples. P-wave detection 974 would be performed by the ED 970. In some examples, Pace detection 976 is performed by the ED, though in other examples, the ED 970 may communicate P-wave timing to the LCP 960 and omit any analysis of P-wave to Pace interval, or in still other examples, the ED may receive pace timing information from the LCP 960 via the communication function 952.

Certain functions 980 may be performed by either the LCP 960 or the ED 970, or may be shared across the two devices. For example, the storage of the desired range 982 for the P-wave to pace interval may be managed by either device 960, 970. In several examples, however, the calculation of the range 982 would be managed by the ED 970. In some examples, an ED may perform such management of the range 982.

The P-wave to Pace interval 984, as outlined above, may be calculated by the ED 970, operating on its own or using data from the LCP 960, or may instead be calculated by the LCP 960 using data communicated from the ED 970. Adjustments 986, which may be performed on the pace-to-pace interval 964 to control P-wave to pace timing, may be calculated by the ED 970 independently or using data communicated from the LCP 960. Adjustments 986 to the pace to pace interval 964 may instead be determined necessary by the ED 970 (with or without data from the LCP 960) and then calculated by the LCP 960 (with or without data from the ED 970). In another example, adjustments 986 to the pace to pace interval 964 may instead by calculated and determined by the LCP 960 using data communicated from the ED 970. As can be readily understood, the system is quite flexible in these respects.

Additional adjustments 986 can also be made to the desired range by, for example, recalculating a desirable P-wave to Pace time interval, as set forth in examples above. In one example, testing may be performed to determine what P-wave to Pace timing achieves a desirable result such as fusion by pacing at various intervals. In another example, pacing may be temporarily halted to calculate an intrinsic P-wave to R-wave interval, allowing calculation using a percentage of the P-R interval of a new desirable P-wave to Pace interval range.

In an alternative, a physician may set the desired range 982 in-clinic using, for example, a patient programmer and surface EKG electrodes to determine a desired range for the P-wave to Pace interval 982, which would then be stored with the LCP 960, such that an ED, such as a wearable device that the physician may never see (i.e. an off-the shelf wearable product), can simply be set up to identify the P-wave and communicate its timing to the LCP 960, making the system 950 operable with any ED 970 that can sense P-waves 974 and communicate to the LCP 960.

In some examples, the LCP may receive a command to deliver a pace at a given interval that is calculated by the extracardiac device. For example, the extracardiac device may issue a command to deliver a pace at a given Pace-to-Pace interval, with the extracardiac device also performing steps to determine the resulting P-wave to Pace interval as discussed herein. Thus block 964 would be performed by the SICD/SCM 970, different from what is shown in FIG. 18. Then, the extracardiac device can adjust its Pace to Pace interval to account for corrections to the P-wave to Pace interval. For such an example, the LCP may not track its own Pace-to-Pace intervals and instead operates as slave to the extracardiac master device. As a result, the extracardiac device 970 may perform each of blocks 964, 982, 984, 986, and uses communication 952 to command pace delivery 962.

A series of illustrative and non-limiting examples follows. These examples are provided for further illumination and is should be understood that other embodiments using other combinations of features are also contemplated.

A first illustrative non-limiting example takes the form of an implantable medical device (IMD) configured for use as part of a cardiac therapy system comprising a leadless cardiac pacemaker (LCP) for delivering pacing therapy and the IMD, the IMD comprising: a plurality of electrodes for sensing cardiac activity; communication circuitry for communicating with the LCP; and operational circuitry configured to receive sensed cardiac signals from the plurality of electrodes and analyze cardiac activity, the operational circuitry comprising: pace timing means to determine when pace therapy is delivered by the LCP; P-wave to Pace means to determine a P-wave to Pace interval by analysis of a segment of the sensed cardiac signals from the plurality of electrodes including a time period prior to pace therapy delivery from the LCP; comparing means to determine whether the P-wave to Pace interval is in a desired range or requires adjustment; and adjustment means to modify a parameter of the pacing therapy delivered by the LCP based on the determination of the comparing means.

An IMD with electrodes as described in the first illustrative non-limiting example is shown, for example, in FIG. 1 at 16 with electrodes 22, 24, 26, and again in FIG. 2 with device 50 and electrodes 64, 66 and 72, and is described above including at least in text associated with these elements. Communication circuitry may include RF, inductive, or conducted communication as described in association with element 62 of FIG. 2. Operational circuitry for the IMD may include, for example, the various circuitry and memory indicated in FIG. 2 at 52, 54, 56, 58 and, optionally, 60, as well as that described above.

Pace timing means may include, for example, executable instructions stored in a memory for operation by a controller, or may include dedicated hardware to perform the cardiac signal monitoring indicated at 810 in FIG. 15, including as needed the use of a search window 814, as well as the analysis indicated at 930 in FIG. 17, or the analysis indicated at 976 of FIG. 18. P-wave to Pace means may include, for example, executable instructions stored in a memory for operation by a controller, or may include dedicated hardware to perform analysis indicated at block 354 of FIG. 7, 820 in FIG. 15, block 942 in FIG. 17, and/or block 984 in FIG. 18, and as described in associated text. The comparing means may include, for example, executable instructions stored in a memory for operation by a controller, or may include dedicated hardware to perform analysis indicated at 830 in FIG. 15, analysis indicated by the analysis circuitry 930 using range 940 and the P-wave to Pace interval 942 of FIG. 17, and assessment of the desired range 982 as compared to the P-pace interval 984 of FIG. 18, and as described in associated text. The adjustment means may include, for example, executable instructions stored in a memory for operation by a controller, or may include dedicated hardware to perform analysis indicated at block 356 in FIG. 7, block 830 in FIG. 15, block 938 in FIG. 17, and block 986 in FIG. 18, and as described in associated text.

A second illustrative and non-limiting example takes the form of an IMD as in the first illustrative and non-limiting example, wherein the operational circuitry further comprises initialization means configured to set the desired range by sensing a one or more intrinsic cardiac cycles, calculating a P-R interval of the patient's cardiac rhythm, and selecting the desired range as a fraction of the P-R interval. Such initialization means may include, for example, executable instructions stored in a memory for operation by a controller, or may include dedicated hardware to perform as indicated at 220 in FIG. 4, which may comprise performing analysis as illustrated and described in association with FIG. 6.

A third illustrative and non-limiting example takes the form of an IMD as in the first illustrative and non-limiting example, wherein the operational circuitry further comprises initialization means configured to set the desired range by sensing a plurality of cardiac cycles paced by the LCP at differing P-wave to Pace intervals, determining which of the plurality of cardiac cycles has been paced in a manner that causes a desired cardiac response; and selecting a the desired range using a P-wave to Pace interval corresponding to the desired cardiac response. Such initialization means may include, for example, executable instructions stored in a memory for operation by a controller, or may include dedicated hardware to perform as indicated at 220 in FIG. 4, which may comprise performing analysis discussed following the description of FIG. 6, above.

A fourth illustrative and non-limiting example takes the form of an IMD as in any of the first to third illustrative and non-limiting examples, wherein the pace timing means is configured to determine when pace therapy is delivered by the LCP by sensing the delivery of pace therapy using the plurality of electrodes. A fifth illustrative and non-limiting example takes the form of an IMD as in any of the first to third illustrative and non-limiting examples, wherein the pace timing means is configured to determine when pace therapy is delivered by the LCP by receiving a communication from the LCP indicating that a pace therapy has been delivered.

A sixth illustrative and non-limiting example takes the form of an IMD as in any of the first to fifth illustrative and non-limiting examples, wherein the P-wave to Pace means comprises data storing means to store a portion of the sensed cardiac signals for retrospective review following a determination that the pace therapy was delivered, and the P-wave to pace means is configured to analyze the segment of the sensed cardiac signals retrospectively using the stored portion. Such storage of signal and searching within a stored segment may include the means described in association with a search window as indicated at 814 in FIG. 15, and as described in associated text.

A seventh illustrative and non-limiting example takes the form of an IMD as in any of the first to sixth illustrative and non-limiting examples wherein the desired range for the P-wave to Pulse interval is set such that the pacing therapy will cause fusion beats.

An eighth illustrative and non-limiting example takes the form of an IMD as in the seventh illustrative and non-limiting example, wherein the IMD comprises initialization means to control the LCP to deliver pacing pulses at a variety of P-wave to Pulse intervals, analyze evoked cardiac response to the pacing pulses delivered at a variety of P-wave to Pulse intervals, and set the desired range to include a range of P-wave to pace intervals that results in fusion beats. Such initialization means may include, for example, executable instructions stored in a memory for operation by a controller, or may include dedicated hardware to perform as indicated at 220 in FIG. 4, which may comprise performing analysis discussed following the description of FIG. 6, above.

A ninth illustrative and non-limiting example takes the form of an IMD as in any of the first to eighth illustrative and non-limiting examples for use in a system where the LCP uses a Pace to Pace interval to control its pacing therapy delivery, wherein the adjustment means is configured to use the communications circuitry to communicate to the LCP to adjust the Pace to Pace interval used by the LCP.

A tenth illustrative and non-limiting example takes the form of an IMD as in the first illustrative and non-limiting example, wherein the LCP is a slave device and the IMD comprises pace control means to use the communication circuitry to command pacing by the LCP according to a pace to pace interval, wherein the adjustment means is configured to adjust the pace to pace interval used by the pace control means.

An eleventh illustrative and non-limiting example takes the form of a subcutaneous implantable defibrillator taking the form of an IMD as in any of the first to tenth illustrative and non-limiting examples and further comprising therapy delivery circuitry configured for delivering defibrillation stimulus to a patient.

A twelfth illustrative and non-limiting example takes the form of a subcutaneous implantable monitoring device taking the form of an IMD as in any of the first to tenth illustrative and non-limiting examples.

A thirteenth illustrative and non-limiting example takes the form of a system comprising an IMD as in any of the first to tenth illustrative and non-limiting examples, and a leadless cardiac pacemaker (LCP), the LCP comprising: a plurality of LCP electrodes for delivering pacing therapy; LCP communication circuitry configured to send and receive messages with the IMD; LCP pacing circuitry for delivering pace therapy using the LCP electrodes according to a Pace to Pace interval parameter; and LCP adjustment means for adjusting the Pace to Pace parameter in response to a communication from the IMD. An LCP as recited is shown and described in association with FIG. 3 including the electrodes 114, 116, 118, 120, communication circuitry shown as module 102, pacing circuitry shown as a pulse generator module 104, and adjustment means that can form executable instructions stored in association with and operable by the processing module 110 and/or dedicated hardware, as desired, to perform functions as indicated at 886 in FIG. 16 and associated text.

A fourteenth illustrative and non-limiting example takes the form of an implantable leadless cardiac pacemaker (LCP) configured to operate in coordination with an extracardiac device (ED), the LCP comprising: a plurality of electrodes for delivering pacing therapy; communication circuitry configured to send and receive messages with the ED; pacing circuitry for delivering pace therapy using the LCP electrodes according to a Pace to Pace interval parameter; P-wave to pace means to receive a message from the ED indicating a time at which a P-wave occurred and determine an interval between the P-wave and a subsequent pace therapy delivery; comparing means to compare the P-wave to Pace to a desired range; and adjustment means to use the result of the comparing means to adjust, as needed, the P-wave to Pace interval by: if the P-wave to pace interval is longer than a first threshold defining the range, to shorten the Pace to Pace interval; or if the P-wave to pace interval is shorter than a second threshold defining the range, to extend the Pace to Pace interval.

For the fourteenth illustrative and non-limiting example, the LCP may be as shown and described in FIGS. 1, 3 and 16 with functions as illustrated in FIGS. 7, 15, and 18, as detailed in association with the thirteenth illustrative and non-limiting example, above. Thus, the P-wave to pace means may include, for example, executable instructions stored in a memory for operation by a controller, or may include dedicated hardware to perform as indicated at 354 in FIG. 6, at block 820 in FIG. 15, as indicated at 890 in FIG. 16, and/or as indicated at 984 in FIG. 18, and as further described in associated text. The comparing means may include, for example, executable instructions stored in a memory for operation by a controller, or may include dedicated hardware to perform as indicated at 830 in FIG. 15, at 888 in FIG. 16 (using analysis circuitry 880), and as indicated at 982 in FIG. 18, and as further described in associated text. The adjustment means may include, for example, executable instructions stored in a memory for operation by a controller, or may include dedicated hardware to perform as indicated at 356 in FIG. 7, 840 in FIG. 15, 886 in FIG. 16, and/or 986 in FIG. 18, and as further described in associated text.

A fifteenth illustrative and non-limiting example takes the form of a system as in the fourteenth illustrative and non-limiting example, wherein the desired range for the P-wave to Pulse interval is set such that the pacing therapy will cause fusion beats.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of providing cardiac pacing therapy to a patient comprising:
   delivering pacing pulses using a Pace to Pace interval, the pacing pulses delivered by a first device which stores the Pace to Pace interval and is configured to deliver at least one of the pacing pulses upon expiration of the Pace to Pace interval after a preceding pacing pulse delivery by the first device;
   monitoring cardiac activity in a second device; and
   adjusting the Pace to Pace interval as stored by the first device in response to communication from the second device to the first device.

2. A method as in claim 1 wherein the step of monitoring cardiac activity in a second device includes identifying a P-wave relative to the at least one of the pacing pulses, and the method further comprises:
   calculating a P-wave to Pace interval using at least the cardiac signals monitored by the second device;
   determining whether the P-wave to Pace interval is in the predetermined range and:
      if the P-wave to pace interval is above the predetermined range, communicating to the first device to shorten the Pace to Pace interval; and
      if the P-wave to pace interval is below the predetermined range, communicating to the first device to extend the Pace to Pace interval.

3. A method as in claim 2 wherein analysis of the P-wave to pace interval is performed by the second device:
   detecting a pace pulse delivered by the first device; and
   searching a predetermined window prior to the detected pace pulse for the P-wave.

4. A method as in claim 2 wherein analysis of the P-wave to pace interval is performed by the second device:
   receiving a communication from the first device indicating at time of delivery of a pace pulse; and
   searching a predetermined window prior to the communicated time of delivery of the pace pulse for the P-wave.

5. A method as in claim 2 wherein analysis of the P-wave to pace interval is performed by the second device:
   detecting an R-wave in the cardiac signal;
   searching a predetermined window prior to the R-wave for the P-wave and finding the P-wave; and
   communicating to the first device a time of the found P-wave.

6. A method as in claim 2 further comprising setting the predetermined range by calculating a P-R interval for an intrinsic cardiac cycle or cycles of the patient and selecting the predetermined range as a fraction of the P-R interval.

7. A method as in claim 2 further comprising setting the predetermined range by:
   delivering a plurality of pacing pulses at a plurality of P-wave to Pace intervals;
   determining which of the plurality of pacing pulses causes a desired cardiac response; and
   selecting a target P-wave to Pace interval corresponding to the desired cardiac response.

8. The method as in claim 7 wherein the desired cardiac response is a fusion beat.

9. A method as in claim 1 wherein the first device is a leadless cardiac pacemaker implanted in or on the left ventricle of the patient's heart, and the second device is a subcutaneous implantable defibrillator.

10. A method as in claim 1 wherein the first device is a leadless cardiac pacemaker implanted in or on the left ventricle of the patient's heart, and the second device is a subcutaneous implantable cardiac monitor.

11. An implantable medical device (IMD) configured for use as part of a cardiac therapy system comprising a leadless cardiac pacemaker (LCP) and the IMD, the IMD comprising:
   a plurality of electrodes for sensing cardiac activity; and operational circuitry configured to receive sensed cardiac signals from the plurality of electrodes and analyze cardiac activity as follows:

determine when pace therapy is delivered by the LCP;

analyze a segment of the sensed cardiac signals from the plurality of electrodes including a time period prior to pace therapy delivery by the LCP and calculate a P-wave to Pace interval;

determine whether the P-wave to Pace interval is in a desired range, and, if the P-wave to Pace interval is not in the desired range, modifying a Pace to Pace interval that determines timing of the LCP pacing therapy.

12. An IMD as in claim 11 wherein the operational circuitry is further configured to set the desired range by sensing a one or more intrinsic cardiac cycles, calculating a P-R interval of the patient's cardiac rhythm, and selecting the desired range as a fraction of the P-R interval.

13. An IMD as in claim 11 wherein the operational circuitry is further configured to set the desired range by sensing a plurality of cardiac cycles paced by the LCP at differing P-wave to Pace intervals, determining which of the plurality of cardiac cycles has been paced in a manner that causes a desired cardiac response; and selecting a the desired range using a P-wave to Pace interval corresponding to the desired cardiac response.

14. The IMD of claim 11 wherein the operational circuitry is further configured to store a portion of the sensed cardiac signals for retrospective review following a determination that the pace therapy was delivered, and to analyze the segment of the sensed cardiac signals retrospectively using the stored portion.

15. The IMD of claim 11 wherein the desired range for the P-wave to Pulse interval is set such that the pacing therapy will cause fusion beats.

16. The IMD of claim 11 wherein the operational circuitry is configured to communicate an adjustment to a Pace to Pace interval to modify the therapy parameter of the LCP.

17. An implantable leadless cardiac pacemaker (LCP) configured to operate in coordination with an extracardiac device (ED), comprising a plurality of electrodes for delivering pacing therapy; communication circuitry configured to send and receive messages with the ED;

and operational circuitry configured to:

deliver a pacing pulse using a Pace to Pace interval relative to a previously delivered pacing pulse;

receive a message from the ED indicating a time at which a P-wave occurred in relation to a paced cardiac event;

calculate a P-wave to Pace interval for the paced cardiac event;

analyze the P-wave to Pace interval relative to a desired range; and:

if the P-wave to pace interval is longer than a first threshold defining the range, shorten the Pace to Pace interval; or if the P-wave to pace interval is shorter than a second threshold defining the range, extend the Pace to Pace interval.

18. The LCP of claim 17 wherein the desired range for the P-wave to Pulse interval is set such that the pacing therapy will cause fusion beats.

19. An implantable medical device system comprising an LCP as in claim 17, and an ED comprising a plurality of electrodes for sensing cardiac activity and communications circuitry for communicating with the LCP; wherein the LCP is configured to communicate to the ED to indicate a time at which a Pace therapy is to be delivered, and, in response thereto, the ED is configured to set a window for sensing the P-wave in order to communicate a time at which the P-wave occurred to the LCP.

20. An implantable medical device system comprising an LCP as in claim 17, and an ED comprising a plurality of electrodes for sensing cardiac activity and communications circuitry for communicating with the LCP; wherein the ED is configured to detect a pacing pulse delivered by the LCP and maintain a memory storing cardiac activity such that the ED can search a time period prior to the detected pacing pulse to identify the P-wave in order to communicate a time at which the P-wave occurred to the LCP.

* * * * *